US005695751A

United States Patent [19]
Friedman et al.

[11] Patent Number: 5,695,751
[45] Date of Patent: *Dec. 9, 1997

[54] ENHANCING DELIVERY OF LARGE NEUTRAL AMINO ACID DRUGS

[75] Inventors: Henry S. Friedman, Durham; Darell D. Bigner, Mebane, both of N.C.; Owen W. Griffith, Milwaukee, Wis.

[73] Assignees: Cornell Research Foundation, Inc., Ithaca, N.Y.; Duke University, Durham, N.C.

[*] Notice: The term of this patent shall not extend beyond the expiration date of Pat. No. 5,407,672.

[21] Appl. No.: 531,586

[22] Filed: Sep. 21, 1995

Related U.S. Application Data

[63] Continuation-in-part of Ser. No. 301,769, Sep. 7, 1994, Pat. No. 5,523,084, which is a continuation-in-part of Ser. No. 46,866, Apr. 8, 1993, Pat. No. 5,407,672.

[51] Int. Cl.$^6$ ............... A61K 38/44; A61K 31/195
[52] U.S. Cl. ............. 424/94.4; 424/94.1; 424/146.1; 424/542; 514/564
[58] Field of Search ............ 424/94.4, 94.1, 424/146.1, 542; 514/564

[56] References Cited

U.S. PATENT DOCUMENTS

| | | | |
|---|---|---|---|
| 4,772,632 | 9/1988 | Vistica | 514/561 |
| 4,997,651 | 3/1991 | Poole et al. | 424/422 |
| 5,075,108 | 12/1991 | McKenzie et al. | 424/85.9 |

FOREIGN PATENT DOCUMENTS

WO 94/23741  10/1994  WIPO.

OTHER PUBLICATIONS

Rich, J. N., et al, Cancer Chemother Pharmacol, 36, 379–384 (1995).
Wellner, D., et al, Fed. Proc. 31, p. 921, abstract 4019 (1972).
Friedman, H.S., et al, Proceedings of the American Association for Cancer Research, vol. 32, p. 318 Abstract 1886 (Mar. 1991).
The Merck Index, 11th edition, pp. 68 and 914 (1989).
Wellner, D., et al, J. Biol. Chem. 235, 2013–2108 (1960).
Barlogie, B., et al, Blood, vol. 67, No. 5 (May), 1298–1301 (1986).
Groothuis, D. R., et al, Cancer Research 52, 5590–5596 (Oct. 1992).
Momma, S, et al, Proceedings of AACR, vol. 26, p. 357, abstract #1408 (Mar. 1985).
Sarosy, G., et al, J. Clin. Oncol., vol. 6, No. 11, 1768–1782 (Nov. 1988).
Bloom, H. J. G., et al, Int. J. Radiation Oncology Biol. Phys., vol. 8, 1083–1113 (1982).
Horowitz, M. E., J. of Clin. Oncol., vol. 6, No. 2, 308–314 (Feb. 1988).
Houghton, J. A., Cancer Treatment Reports, vol. 69, No. 1, 91–96 (Jan. 1985).
Vistica, D. T., Proceedings of AACR and ASCO, vol. 18, p. 26, abstract #104, 1977.
Cornford, E. M., et al, Cancer Research 52, 138–143 (Jan. 1992).
Friedman, H. S., Cancer Research 46, 224–228 (Jan. 1986).
Leff, R. S., et al, J. Clin. Oncol., vol. 4, No. 11, 1586–1591 (Nov. 1986).
Prichard, J., et al, Br. J. Cancer, 45, 86–94 (1982).
Vistica, D. T., et al, Cancer Letters, 6, 345–350 (1979).
Moynihan, M. K., et al, Proceedings of AACR, vol. 36, p. 374, Abstract No. 2230 (Mar. 1995).
Friedman, H. S., et al, Cancer Research 46, 2827–2833 (Jun. 1986).
Friedman, H. S., et al, Cancer Research 48, 3189–4195 (Aug. 1988).
Rich, J. N., et al, Proceedings of AACR, vol. 34, p. 299, abstract No. 1778, dated Mar. 1993.
Ahluwalia, G. S., et al, Pharm. Ther., vol. 46, pp. 243–271 (1990).
Halperin, E. C., et al, Int. J. Radiation Oncology Biol. Phys., vol. 24, 103–109 (1992).
Goldenberg, G. J., et al, Cancer Research 30, 2285–2291 (Sep. 1970).
Goldenberg, G. J., et al, Cancer Research 37, 755–760 (Mar. 1977).
Goodman and Gilman's The Pharmacological Basis of Therapeutics, 8th edition, 1202–1208 (1975).
Pardridge, W. M., et al, Federation Proceedings, 45, 2073–2078 (Jun. 1986).
Li, Jia–He, et al, J. Med. Chem., 38, 1955–1965 (1995).
Lippitz, B. E., et al, Neurosurgery 26, 255–260 (1990).
Zaharko, D. et al., Cancer Research, vol. 52(3), pp. 3604–3609, Jul. 1992.
Rich, J.N. et al., Cancer Chemother. Pharmacol., vol. 36(5), pp. 379–384, 1995.

*Primary Examiner*—Chhaya D. Sayala

[57] ABSTRACT

L-amino acid oxidase is utilized to reduce the plasma level of large neutral amino acids to allow the opportunity of increased large neutral amino acid drug transport across the blood brain barrier. Preferably anti L-amino acid oxidase antibody is administered intermediate to the L-amino acid oxidase and large neutral amino acid drug administrations to deplete L-amino acid oxidase activity once the L-amino acid oxidase has caused the large neutral amino acid drug transport improving level plasma reduction of large neutral amino acids thereby to reduce or eliminate degrading of large neutral amino acid drugs by L-amino acid oxidase. The large neutral amino acid drugs include levodopa, melphalan, L-DON, azaserine, acivicin, L-alanosine and 3-(phosphonomethyl)phenylalanines. For treatment of brain tumors, the drug administration is preferably preceded by the administration of a large neutral amino acid glutathione depleting agent, e.g., L-buthionine-SR-sulfoximine. L-Amino acid oxidase is also utilized to enhance the transport of large neutral amino acid glutathione depleting agent across the blood brain barrier as an adjunct to radiation therapy of brain tumors.

22 Claims, 4 Drawing Sheets

ENHANCING DELIVERY OF LARGE NEUTRAL AMINO ACID DRUGS

CROSS-REFERENCE TO RELATED APPLICATION

This is a continuation-in-part of Ser. No. 08/301,769, filed Sep. 7, 1994 now U.S. Pat. No. 5,523,089, which, in turn, is a continuation-in-part of Ser. No. 08/046,866, filed Apr. 8, 1993, now U.S. Pat. No. 5,407,672.

The invention was made at least in part with Government support under National Institutes of Health grant numbers DK 26912, NS 20023 and CA 11898. The Government has certain rights in the invention.

TECHNICAL FIELD

The invention herein is directed to enhancing the delivery of large neutral amino acid drugs and large neutral amino acid glutathione depleting agents in the treatment of diseases where crossing the blood-brain barrier by the drugs and/or agents is necessary.

BACKGROUND OF THE INVENTION

Melphalan, (4-[bis(2-chloroethyl)amino]-L-phenylalanine), is a nitrogen mustard that is useful as a chemotherapeutic agent. Goodman and Gilman's The Pharmaceutical Basis of Therapeutics, 8th edition, pages 1202–1208 (1990) classifies melphalan as an alkylating agent type of chemotherapeutic action and indicates a mechanism of action of cross-linking DNA. Sarosy, G., et al, Journal of Clinical Oncology, Vol. 6, No. 11 (November), pp. 1768–1782 (1988) indicates that melphalan effects cytotoxicity by forming either interstrand, intrastrand, or DNA-protein cross links.

The wide spectrum of melphalan's anti-neoplastic activity against tumors, in vivo, is reported in the literature. Goodman and Gilman's The Pharmaceutical Basis of Therapeutics, 8th edition, pages 1202–1208 (1990) indicates that melphalan is currently used in the treatment of multiple myeloma, breast cancer and ovarian cancer. Sarosy, G., et al, Journal of Clinical Oncology, Vol. 6, No. 11 (November), pp. 1768–1782 (1988), a review article on intravenous melphalan usage, at page 1772 in Table 1 indicates that at lower doses intravenous melphalan demonstrated at least some activity against pancreatic cancer, colon carcinoma, medulloblastoma, rhabdomyosarcoma, osteosarcoma, and ovarian cancer; at page 1774 in Table 3 indicates that at higher dosages intravenous melphalan demonstrated at least some activity against breast cancer, non-small-cell lung cancer, small-cell lung cancer, colon cancer, melanoma, testicular cancer, ovarian cancer, soft tissue sarcoma, Ewing's sarcoma, synovial cell sarcoma, bone (giant cell) sarcoma, Wilms' sarcoma, Wilms' osteogenic sarcoma, rhabdomyosarcoma, multiple myeloma, neuroblastoma, Hodgkin's lymphoma, non-Hodgkin's lymphoma, acute lymphocytic leukemia, acute nonlymphoblastic leukemia, chronic granulocytic leukemia and renal cancer and characterizes the response rate for melanoma and colon carcinoma as extraordinarily high; at page 1773, Table 2 indicates that drug combinations including low dosages of intravenous melphalan demonstrated at least some activity against ovarian cancer, testicular cancer, non-small-cell lung cancer, melanoma and multiple myeloma; and at pages 1776–177, Table 4 indicates that drug combinations including higher dosages of intravenous melphalan demonstrated at least some activity against neuroblastoma, melanoma, non-Hodgkin's lymphoma, Hodgkin's lymphoma, Burkett's lymphoma, CML-blast crises, multiple myeloma, colonic cancer, breast cancer, sarcoma and gastric cancer. Barlogie, B., et al, Blood, Vol. 67, No. 5 (May), 1298–1301 (1986), indicates that large doses of melphalan demonstrated activity against advanced multiple myeloma. Horowitz, M. E., et al, Journal of Clinical Oncology, Vol. 6, No. 2 (February), 308–314 (1988), indicates that melphalan demonstrated partial responses in 10 of 13 patients having newly diagnosed, poor-risk rhabdomyosarcoma. Houghton, J. A., et al, Cancer Treatment Reports, Vol. 69, No. 1, 91–96 (January 1985), indicates that melphalan demonstrated complete regressions in 6 of 7 lines of childhood rhabdomyosarcomas. Leff, R. S., et al, Journal of Clinical Oncology, Vol. 4, No. 11 (November), pp. 1586–1591 (1986), indicates that high-dose melphalan demonstrated complete responses in 15% of cases of metastatic colon cancer and partial responses in 30% of cases of metastatic colon cancer. Pritchard, J., et al, Br. J. Cancer, 45, 86–94 (1982), indicates that high dose melphalan demonstrated complete response in 6 of 11 of certain patients with advanced neuroblastoma.

With cells grown in culture, melphalan has been shown to be effective against brain tumors, including gliomas, and medulloblastomas. See Friedman, H. S., et al, Cancer Research 46, 2817–2838, June 1986 and Friedman, H. S., et al, Cancer Research 48, 4189–4195, August 1988 on the experimental chemotherapy of human medulloblastoma cell lines.

It has been discovered that starving followed by a protein-free diet reduces plasma levels of amino acids including large neutral amino acids and increases the blood-to-tumor periphery tissue transfer constant of melphalan both for subcutaneous tumors (representative of all tumors except for brain tumors) and also for brain tumors. See Friedman, H. S., et al, Proceedings of the American Association for Cancer Research, Volume 32, page 318, Abstract 1886, March, 1991 and Groothius, D. R., et al, Cancer Research 52, 5590–5596 (Oct. 15, 1992). This increase of blood-to-tumor tissue transfer constant might be expected to allow use of lesser dosages of melphalan (and concomitant reduced toxicity) in circumstances where melphalan is now considered useful and the extension of use of melphalan in circumstances now foreclosed by the blood brain barrier, i.e., as an antitumor agent against brain (intracranial) tumors. However, the accomplishment of this by means of starving and administration of a protein free diet affords at most limited improvement.

The finding that reduced plasma levels of large neutral amino acids were associated with increased blood-to-tumor melphalan transfer constants is consistent with previous work showing that melphalan is transported by the same transport system as the large neutral amino acids and that the presence of large neutral amino acids in plasma interferes with the transport of melphalan. Thus achieving reduction of plasma levels of large neutral amino acids by means different from or additional to restricted diet to the same or greater degree as is obtained with said restricted diet, should improve melphalan transport and result in a benefit if said different means doesn't concurrently provide deleterious effect.

Various enzymes are known for which large neutral amino acids are substrates and which would be useful for reducing plasma levels of these provided they have access to required cosubstrates. However, melphalan is also a large neutral amino acid and would likely be a substrate for the same enzymes. Furthermore, the various possible enzymes would be expected to differ in respect to the number of different large neutral amino acids that would be substrates and in their relative kinetic constants vis-a-vis their large neutral amino acid substrates and melphalan. Therefore, such enzymes might be expected, on the one hand, to potentiate the transport of melphalan into tumors by reducing plasma concentrations of large neutral amino acids, but on the other hand, would be expected to act in counterproductive fashion if still present upon melphalan administration by degrading melphalan to an extent which might be larger than the extent of increased melphalan transport from large neutral amino acid depletion. Furthermore, each particular enzyme might be expected to have a different effect on concentrations of plasma large neutral amino acids and degradation of melphalan.

What is necessary is selection of an enzyme which will reduce plasma large neutral amino acids to enhance melphalan transport but which would be relatively less active toward melphalan or which would or could be sufficiently inactivated, within the period of reduced plasma amino acid level, so as not to degrade the melphalan to an extent of negating the benefit obtained by enhanced melphalan transport. For any particular enzyme, there is no expectation of success of meeting these criteria.

Moreover, there are other large neutral amino acid drugs which are administered for treatment of diseases where crossing the blood-brain barrier is necessary for the treatment. The question is presented whether the delivery across the blood-brain barrier of large neutral amino acid drugs generally can be enhanced by reducing plasma levels of large neutral amino acids and, if so, how this can be effected to accomplish enhanced delivery without degrading the administered drug to an extent of negating the benefit obtained by enhanced drug transport.

SUMMARY OF THE EMBODIMENTS OF THE INVENTION

It has been discovered herein that administration of L-amino acid oxidase successfully enhances the transport of large neutral amino acid drugs across the blood brain barrier to obtain improved effect in the treatment of brain associated diseases, and when accompanied by fasting and/or a protein restricted diet provides improved efficacy over fasting and protein restricted diet alone. In contrast to starving which reduces the plasma level of essentially all amino acids, use of L-amino acid oxidase reduces the plasma level of only amino acids that are actively degraded by L-amino acid oxidase and provides α-ketoacid reaction products which are eventually converted back to amino acids in the body or are catabolized intracellularly for energy.

It has been discovered herein that improved effect is obtained by utilizing L-amino acid oxidase to reduce plasma level of large neutral amino acids to allow the opportunity of increased large neutral amino acid drug transport across the blood brain barrier and then capitalizing on this opportunity by administering large neutral amino acid drug when the plasma level of L-amino acid oxidase activity is sufficiently low so the gain from increased transport outweighs the loss from L-amino acid oxidase-mediated metabolism of large neutral amino acid drug, preferably with the intermediate administration of anti L-amino acid oxidase antibody to deplete L-amino acid oxidase activity once the L-amino acid oxidase has caused the large neutral amino acid drug transport improving plasma level reduction of large neutral amino acids thereby to reduce or eliminate the degrading effect of L-amino acid oxidase on large neutral amino acid drug.

The method of a first embodiment herein is directed to treating a patient (human or animal) for a brain associated disease with a large neutral amino acid drug where crossing the blood brain barrier by the drug is necessary for the treatment and comprises the steps of (a) administering L-amino acid oxidase to said patient at a dosage ranging from about 1 to about 100 units/ml of plasma (corresponding to about 85 to about 8500 units/kg of body weight), which is non-toxic and which is sufficient to reduce plasma level of large neutral amino acids from a normal level to a large neutral amino acid drug transport improving level;

(b) administering therapeutically effective amount of the large neutral amino acid drug to the patient wherein plasma level of large neutral amino acids is reduced from normal level within about 2 to 36 hours after administering L-amino acid oxidase.

In a preferred execution of this first embodiment, the L-amino acid oxidase is administered in step (a) at a dosage ranging from about 10 units/ml to about 50 units/ml and the administration of step (b) is carried out from 12 to 30 hours after the administration of step (a).

In a very preferred execution of this first embodiment, the method comprises preventing replenishment of large neutral amino acids to plasma during the period between the administration of step (a) and the administration of step (b) and optimally also during the period of drug uptake by causing the patient to fast or by administering a protein-free diet or by causing the patient to fast followed by administering a protein-free diet.

The method of a second embodiment herein is directed to treating a patient (human or animal) for a brain associated disease with a large neutral amino acid drug where crossing the blood brain barrier by the drug is necessary for the treatment and comprises the steps of (a) administering L-amino acid oxidase to said patient at a dosage ranging from about 1 to about 100 units/ml of plasma (corresponding to about 85 to about 8500 units/kg of body weight), which is non-toxic and which is sufficient to reduce plasma level of large neutral amino acids from a normal level to a large neutral amino acid drug transport improving level;

(b) administering to the patient wherein the plasma level of large neutral amino acids is reduced from normal level and from about 1 to 30 hours after the administering in step (a), from about 1 to about 25 μg anti L-amino acid oxidase antibody per unit of L-amino acid oxidase administered in step (a), to inhibit plasma L-amino acid oxidase activity so that plasma L-amino acid oxidase activity is less than 25% of the plasma L-amino acid oxidase activity one hour after the administration of step (a), this reduction in plasma L-amino acid oxidase activity being caused by the combination of anti L-amino acid oxidase antibody caused inhibition and metabolism of L-amino acid oxidase unrelated to anti L-amino acid oxidase antibody administration.

(c) administering therapeutically effective amount of the large neutral amino acid drug to the patient wherein plasma level of large neutral amino acids is reduced from normal level, within about 1 to 10 hours after the administering in step (b) and within about 2 to 36 hours after the administering in step (a).

In a preferred execution of the method of the second embodiment, the L-amino acid oxidase is administered in step (a) at a dosage ranging from 10 units/ml to about 50 units/ml, the anti L-amino acid oxidase antibody is administered in step (b) at a dosage ranging from about 1 to about 5 μg anti L-amino acid oxidase antibody per unit of L-amino acid oxidase administered in step (a), the administration in step (b) is carried out from about 1½ to about 6 hours after the administration of step (a) and the administration of step (c) is carried out from about 1 to 10 hours after the administration of step (b) and about 2½ to 20 hours after the administering in step (a).

The term "large neutral amino acid drug" is used herein to mean drug which is transported by the neutral amino acid transport system and which is metabolized by L-amino acid oxidase. The neutral amino acid transport system is described in Pardridge, W. H., et al, Federation Proceedings, Vol. 45, No. 7, 2073–2078 (June 1986).

The term "brain associated disease" is used herein to mean a disease or disorder for which treating agent needs to be delivered to the central nervous system and includes hypokinetic movement disorders such as idiophathic Parkinson's disease, postencephalitic parkinsonism and symptomatic parkinsonism; and acute ischemia events such as stroke or cerebral trauma; and neurodegenerative disorders besides hypokinetic movement disorders, such as Alzheimer's disease, Huntington's disease, human immunodeficiency virus related injury and amyotrophic lateral sclerosis; and a brain tumor susceptible to DNA cross-linking cytotoxicity or to cellular nucleotide synthesis interruption cytotoxicity or to AMP, ATP, dATP and DNA biosynthesis interruption. Brain tumors susceptible in all three cases include gliomas, ependymomas, pineoblastomas, germinomas, medulloblastomas, non germinoma germ cell tumors, primitive neuro ectodermal tumors (PNET), anaplastic astrocytomas, choroid plexus carcinomas and rhabdoid tumors.

In embodiments herein where patients with brain tumors are treated with large neutral amino acid drug, the administration of the large neutral amino acid drug is preferably preceded by administration of a glutathione depleting effective amount of a large neutral amino acid glutathione depleting agent which is not metabolized by L-amino acid oxidase. Glutathione depletion caused thereby makes the brain tumor more susceptible to the cytotoxic effects of the large neutral amino acid drug.

It has been discovered herein that administration of L-amino acid oxidase successfully enhances the transport of large neutral amino acid glutathione depleting agents across the blood brain barrier when they are used to reduce the radiation therapy requirement in the treatment of brain tumors susceptible to radiation therapy, e.g., the brain tumors mentioned above.

An embodiment relying on this discovery, denoted the third embodiment herein, is directed to a method of treating a patient (human or animal) for a brain tumor which is susceptible to radiation therapy comprising:

(a) on a daily basis, administering L-amino acid oxidase to said patent at a dosage ranging from about 1 to 100 units/ml of plasma (corresponding to about 85 to about 8,500 units/kg of body weight) which is non-toxic and which is sufficient to reduce plasma level of large neutral amino acids from a normal level to a large neutral amino acid glutathione depleting agent transport improving level and administering to the patient wherein the plasma level of large neutral amino acids is reduced from normal level and from about 1½ to 6 hours after the administration of the L-amino acid oxidase from 20 to 80 mg/kg of large neutral amino acid glutathione depleting agent which is not metabolized by L-amino acid oxidase, and continuing this treatment for as many days as is necessary to deplete glutathione in said tumor, (b) administering radiation therapy in a tumor volume reducing amount to said tumor wherein glutathione has been depleted.

The term "large neutral amino acid glutathione depleting agent" is used herein to mean a large neutral amino acid which when administered to a patient causes glutathione depletion in the patient.

One unit of L-amino acid oxidase is that amount which converts 1 μmol of L-leucine to α-ketoacid reaction product per minute at 37° C. and corresponds approximately to 0.01 mg of crystalline L-amino acid oxidase.

The term "plasma level of large neutral amino acids" is used herein to mean the plasma level of the amino acids histidine, leucine, isoleucine, methionine, phenylalanine, tryptophan, tyrosine and valine.

The term "normal level" of large neutral amino acids is used herein to mean the total concentration of the amino acids histidine, leucine, isoleucine, methionine, phenylalanine, tryptophan, tyrosine and valine found in plasma in a patient (human or animal) not experiencing dietary restriction or supplementation.

The terms "large neutral amino acid drug transport improving level" and "large neutral amino acid glutathione depleting agent transport improving level" are used herein to mean a concentration of the amino acids histidine, leucine, isoleucine, methionine, phenylalanine, tryptophan, tyrosine and valine in plasma in a patient (human or animal) that allows large neutral amino acid drug transport and large neutral amino acid glutathione depleting agent transport across the blood brain barrier to be improved relative to the extent of large neutral amino acid drug transport across the blood brain barrier that would be observed in the absence of L-amino acid oxidase treatment and plasma large neutral amino acid depletion. Such improved transport is manifested by better treatment results with the same dosage of drug or agent or the same treatment results on administration of a lesser amount of the drug or agent.

Amino acids can be qualified using standard techniques on a model 7300 amino acid analyzer (Beckman Instruments, Inc., Palo Alto, Calif.).

The term "anti L-amino acid oxidase antibody" is used herein to mean any antibody to L-amino acid oxidase obtained by immunizing a mammal with L-amino acid oxidase, recovering serum containing said antibody from the mammal typically 30 to 60 days after immunization and preferably purifying the antibody from the serum, or monoclonal antibody corresponding thereto.

Anti L-amino acid oxidase antibodies can be quantified by the enzyme-linked immunosorbent method as described in Example IX.

DETAILED DESCRIPTION OF THE INVENTION

Figure 1:
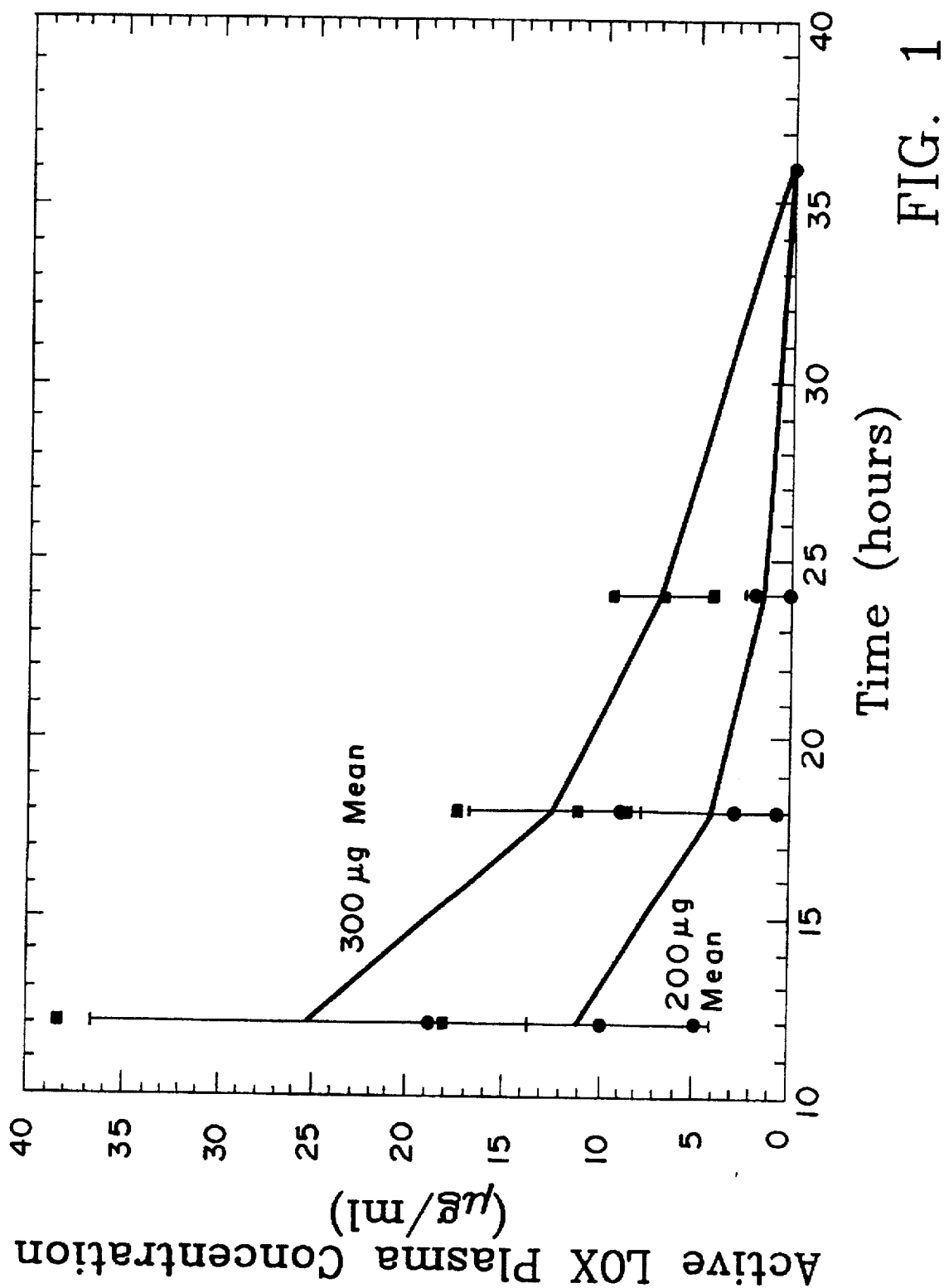
FIG. 1 depicts graphs of L-amino acid oxidase plasma concentration (denoted "Active LOX Plasma Concentration") vs. time after intravenous treatment of mice with 200 and 300 μg of L-amino acid oxidase, based on data determined in Example II.

We turn firstly to the large neutral amino acid drugs which are administered in the methods herein.

One such drug is levodopa. It is used in the methods herein, with or without administration of carbidopa, in a therapeutically effective amount for treatment of idiopathic Parkinson's disease, postencephalitic parkinsonism and symptomatic parkinsonism which may follow injury to the nervous system by carbon monoxide intoxication or manganese intoxication. The dosage of levodopa/carbidopa can range from 300/75 to 2500/250 mg/day with administration carried out orally. Initially, a 100/25 mg/day tablet is given and this dosage is gradually increased to maximize results. When levodopa is utilized without carbidopa, the dosage of levodopa utilized to obtain the same results typically needs to be 33 to 50% greater than when it is used in combination with carbidopa. In the invention herein,the dosage of levodopa utilized preferably is 40 to 60% of that normally used, i.e., 40 to 60% of the dosage without prior L-amino acid oxidase administration.

Another such drug is melphalan. It is administered in an anti-tumor effective amount for treatment of a patient for a brain tumor which is susceptible to DNA cross-linking caused cytoxicity and which is therefore susceptible to melphalan, including the brain tumors mentioned above in the paragraph about "brain associated disease." Normally, the dosage ranges from about 2 to 120 mg/kg of body weight (corresponding to about 6 to 360 mg/square meter of body surface). Preferably, the dosage ranges from about 5 to 70 mg/kg of body weight (corresponding to about 15 to 210 mg/square meter of body surface), very preferably from 11.8 to 23.7 mg/kg (corresponding to about 35.5 to 71 mg/square meter of body surface). In the invention herein, the dosage of melphalan utilized is preferably 40 to 60% of that normally used, i.e., 40 to 60% of the dosage without prior administration of L-amino acid oxidase. Conventionally, melphalan is administered orally. This is a suitable method for administration in both embodiments herein and is a preferred method of administration when the execution relying on PEG-modified L-amino acid oxidase, as described later, is utilized. However, when L-amino acid oxidase in unmodified form is administered parenterally or is administered via an extra corporeal reactor, the melphalan is preferably administered parenterally, very preferably intravenously as a bolus injection.

Large neutral amino acid drugs besides L-melphalan whose transport may be improved on use in place of melphalan in the methods herein include sarcolysin (D,L-melphalan); medphalan (D-melphalan); meta-sarcolysin, which is 3-[m-(bis-(2'-chloroethyl)amino)]-D,L-phenylalanine;and aminochlorambucil, which is a higher homolog of melphalan; and in general nitrogen mustards of any of the large neutral amino acids mentioned herein.

A class of large neutral amino acid drugs herein are large neutral amino acid L-glutamine antagonists. These are administered in an anti-tumor effective amount for treatment of a brain tumor which is susceptible to cellular nucleotide synthesis interruption cytotoxicity and which is therefore susceptible to these drugs, e.g., the brain tumors mentioned above in the paragraph about "brain associated disease." The large neutral amino acid L-glutamine antagonists include 6-diazo-5-oxo-L-norleucine (L-DON), O-diazoacetyl-L-serine also known as azaserine and L-[αS,5S]-α-amino-3-chloro-4,5-dihydro-5-isoxazoleacetic acid also known as acivicin. These three drugs are described in Ahluwalia, G. S., et al, Pharmac. Ther., Vol. 16, 243–271 (1990). For L-DON, the dosage normally ranges from 0.1–1.1 mg/kg/day for oral administration and from 0.2–0.6 mg/kg/day for intramuscular or intravenous administration. For azaserine, the dosage normally ranges from 5 to 10 mg/kg/day for oral administration and from 5 to 10 mg/kg/day for intramuscular or intravenous administration. For acivicin, the dosage normally ranges from 12–25 mg/square meter of body surface per day and administration is carried out intravenously as a bolus injection or by continuous infusion.

Another class of large neutral amino acid drugs herein are large neutral amino acid N-methyl-D-aspartate receptor antagonists. These include S-configuration and R,S-configuration, 3-(phosphonomethyl) phenylalanine optionally substituted at the 2-position, for example, with nitro and at the 5-position, for example, with phenyl, 1-naphthyl, or 2-naphthyl. The 3-(phosphonomethyl) phenylalanines and their preparation are described in Li, J.-H, et al J. Med. Chem. 38, 1955–1965 (1995). For treating acute ischemic events such as stroke or cerebral trauma, they are administered in a neuroprotective amount. For treating neurodegenerative disorders such as Parkinson's disease, Alzheimer's disease, Huntington's disease, human immunodeficiency virus related injury and amyotrophic lateral sclerosis, they are administered in an anticonvulsant on tremor suppressing amount. The dosage generally ranges from 0.1 to 100 mg/kg and administration can be carried out orally or parenterally, very preferably intravenously as a bolus injection or a continuous infusion.

Another large neutral amino acid drug for use herein is the L-aspartic acid analog L-alanosine. It is administered in an anti-tumor effective amount for treatment of a brain tumor which is susceptible to AMP, ATP, dATP and DNA biosynthesis interruption, e.g., the brain tumors mentioned above in the paragraph about "brain associated disease." The dosage for L-alanosine normally ranges from 100 to 4,000 mg/m$^2$ and administration is carried out by any parenteral route, e.g., intravenously as a bolus injection or by continuous infusion.

We turn now to the first embodiment of the invention herein.

L-Amino acid oxidase is a flavoprotein that catalyzes the oxidative deamination of certain L-amino acids to the corresponding α-keto acids. It occurs in many snake venoms (e.g., the venom of the eastern diamondback rattlesnake) and is isolated therefrom as described in Wellner, D., et al, J. Biol. Chem. 235,2013 (1960). For its use herein, the L-amino acid oxidase should be pure, i.e., free of all of the toxins and other enzymes present in the snake venom from which it is isolated. The required purification is accomplished, for example, by isolating the compound in crystallized form by dissolving 1 gm lyophilized snake venom (Miami Serpentarium) in 100 ml water, adding 10 ml of 100 mM L-leucine, heating under $N_2$ to 70° C. for 5 minutes, centrifuging to remove precipitated protein, mixing the supernatant solution with 400 mg (dry weight) of hydroxyapatite gel, adding HCl to reduce the pH to 5.5, centrifuging to obtain a precipitate of enzyme bound to gel, resuspending the precipitate in 35 ml of 2.3M ammonium sulfate in 80 mM Na acetate buffer, pH 4.6, to release the enzyme from the gel, centrifuging to obtain a supernatant containing enzyme, adding 141 mg/ml of ammonium sulfate to precipitate the enzyme, centrifuging to obtain a pellet of the precipitate, dissolving the pellet in cold water, dialyzing the resulting solution against water at 4° C. to cause crystallization of the L-amino acid oxidase, collecting the crystals by centrifugation, redissolving in 2 ml of 100mM KCl, again dialyzing against water to form crystals and then recrystallizing again. The crystals can be dissolved in physiological saline to give an injectable preparation.

As indicated above, the L-amino acid oxidase is administered at a dosage ranging from about 1 to about 100 units/ml of plasma (corresponding to about 85 to about 8500 units/kg at body weight) which is non-toxic and which is sufficient to reduce plasma level of large neutral amino acids from a normal level to a large neutral amino acid drug transport improving level. The dosage for the L-amino acid oxidase can range, for example, from about 5 to about 25 units/ml of plasma (corresponding to about 425 to about 2125 units/kg of body weight) to reduce plasma level of large neutral amino acids in a patient to a large neutral amino acid drug transport improving level of less than 50% of normal level, and from about 10 to about 50 units/ml of plasma (corresponding to about 850 to about 4250 units/kg of body weight) to reduce plasma level of large neutral amino acids in a patient to a large neutral amino acid drug transport improving level of less than 10% of normal level.

The L-amino acid oxidase can be administered by any parenteral route, e.g., intravenously, intraperitoneally or subcutaneously. A preferred method of administration is intravenous administration.

The L-amino acid oxidase can also be administered to the patient by attaching it to an extracorporeal reactor and passing the patient's blood through the reactor. Said reactor can be a packed bed of Dacron fibers to which L-amino acid oxidase is attached using γ-aminopropyltriethoxysilane and glutaraldehyde (general method of R. Y. C. Ko, et al, J. Biomed. Res., 10, 249–258(1976)) or said reactor may be an insoluble carrier matrix of reconstituted bovine collagen containing L-amino acid oxidase (general method of L. S. Olanoff, et al, J. Biomed. Res., 8, 125–136(1977)) or said reactor may be a conventional hollow-fiber hemodialyzer to which L-amino acid oxidase is attached covalently (general method of J. A. Jackson, et al, J. Pharmacol. Expt. Ther., 209, 271–274(1979)). In each case the patient's blood is passed through the extracorporeal reactor by means of conventional arteriovenous cannulation wherein blood is removed from the patient through an arterial cannula, passed through the extracorporeal reactor and then returned to the patient through a venous cannula. Use of an extracorporeal reactor as described above, and disconnecting it prior to large neutral amino acid drug administration, eliminates the opportunity for L-amino acid oxidase to degrade the drug.

The L-amino acid oxidase is also advantageously administered in methoxypropylene glycol (PEG) modified form, to increase its plasma half-life and to decrease its antigenicity. The PEG utilized is preferably of 5000 daltons. The L-amino acid oxidase and PEG are covalently coupled using 2,4,6-trichloro-s-triazine (general method of K. V. Savoca, et al, Biochem. Biophys. Acta, 578, 47–53(1979)) and PEG is attached to 50% to 60% of the free amino groups of L-amino acid oxidase. L-amino acid oxidase modified in this manner has a circulating half-life more than 10-fold that of unmodified L-amino acid oxidase.

The term "administering L-amino acid oxidase" used herein includes using unmodified L-amino acid oxidase as well as using PEG-modified L-amino acid oxidase and reactor bound L-amino acid oxidase.

Turning now to step (b) of the first embodiment herein, as indicated above the dosage of large neutral amino acid drug administered is a therapeutically effective amount. Dosages for various drugs are discussed above.

As indicated above, administration in step (b) of the first embodiment herein is carried out when the plasma level of large neutral amino acids is reduced from normal level so as to improve the transport of the large neutral amino acid drug across the blood brain barrier. When L-amino acid oxidase is administered parenterally in unmodified form, the administration of step (b) is ordinarily carried out from 2 to 36 hours, very preferably from 12 to 30 hours, after the administration of step (a). When the embodiment is used where L-amino acid oxidase is linked to an extracorporeal reactor, L-amino acid oxidase mediated degradation of large neutral amino acid drug is not a factor and therefore time need not be provided for L-amino acid oxidase inactivation to a level where it will not degrade large neutral amino acid drug to too great an extent; in this case the large neutral amino acid drug is preferably administered at the earlier times in the above range. When the embodiment is used where the L-amino acid oxidase is administered in PEG-modified form, the period for melphalan administration can be shifted to accommodate for the increased effective life of the L-amino acid oxidase, e.g., to range from 12 to 360 hours after administration of L-amino acid oxidase, with large neutral amino acid drug given, in some cases, more than once during that interval.

Preferably the large neutral amino acid drug is administered in step (b) of the first embodiment herein in a therapeutically effective amount to the patient wherein the plasma large neutral amino acids are at the reduced level, when the patient's plasma L-amino oxidase level is such that less than 15% of the large neutral amino acid drug would be metabolized by the L-amino acid oxidase during the period in which large neutral amino acid transport across the blood brain barrier is at least 85% complete. Very preferably, the large neutral amino acid drug is administered when the patient's plasma L-amino acid oxidase level is such that less than 10% of the large neutral amino acid drug would be metabolized by the L-amino acid oxidase during the period in which large neutral amino acid transport across the blood brain barrier is at least 90% complete. The period during which the patient's plasma level is such that metabolizing of large neutral amino acid drug is restricted to the recited degree and large neutral amino acid transport across the blood brain barrier is complete to the recited degree, may be estimated from data on L-amino acid oxidase concentration in plasma versus time after administration, data on the rate of large neutral amino acid drug degradation at any L-amino acid oxidase plasma concentration coupled with the assumption that L-amino acid oxidase mediated large neutral amino acid drug degradation is expected to be directly proportional to the L-amino acid oxidase concentration, and data known from any clinical studies on the time required for large neutral amino acid drug transport across the blood brain barrier to the specified amount of completeness modified by the estimate of reduction of the time as a result of the L-amino acid oxidase treatment.

Routes of administration for various large neutral amino acid drugs are discussed above.

We turn now to the execution of the first embodiment where replenishment of large neutral amino acids to plasma is prevented during the period between the administration of step (a) and the administration of step (b). This can be carried out, for example, by precluding the patient from intake of nutriments providing large neutral amino acids to the plasma essentially all during the period between the administering of step (a) and the administering of step (b), e.g., by causing the patient to fast or by administering a protein-free or protein-restricted diet during said period. Suitable protein-free or protein-restricted diets include, for example, standard total parenteral nutrition solutions formulated to contain no amino acids or to contain no large neutral amino acids, protein-free liquids (e.g., water, soda, coffee), and oral diets containing only carbohydrates and fats. In a preferred embodiment, the patient is caused to fast for 15 to 20 hours after the administration of step (a) and the fasting is followed by administration of protein-free diet (e.g., amino acid-free total parenteral nutrition solutions or other alternatives recited hereinbefore) for 4 to 8 hours with the latter providing sustainment for the subsequent large neutral amino acid drug administration and to mitigate sickness being caused by the fasting, and very preferably, the protein-free diet is continued for up to 4 hours after large neutral amino acid drug administration so the plasma large neutral amino acids are not replenished prior to the uptake of the large neutral amino acid drug.

We turn now to the second embodiment of the invention herein, i.e., the embodiment where anti L-amino acid oxidase antibody is administered between L-amino acid oxidase administration and large neutral amino acid drug administration to deplete L-amino acid oxidase activity once the L-amino acid oxidase has caused the large neutral amino acid drug transport improving plasma level reduction of large neutral amino acids so as to reduce or eliminate degrading of administered large neutral amino acid drug caused by administered L-amino acid oxidase.

We turn firstly to step (a) of the second embodiment.

Step (a) in the second embodiment herein is the same as step (a) in the first embodiment herein and the same detailed description recited above for step (a) for the first embodiment is appropriate for the second embodiment herein except that administration utilizing an extracorporeal reactor is not appropriate for the second embodiment herein.

We turn now to step (b) of the second embodiment.

As indicated above, this step comprises administering to the patient wherein the level of large neutral amino acids is reduced from normal level and from about 1 to 30 hours after the administering in step (a), from about 1 to 25 µg anti L-amino acid oxidase antibody per unit of L-amino acid oxidase administered in step (a), to inhibit plasma L-amino acid oxidase activity.

As indicated above, the anti L-amino acid oxidase antibody is obtained by immunizing mammal with L-amino acid oxidase, recovering serum containing said antibody from the mammal, typically 30 to 60 days after immunization and preferably purifying the antibody from the serum, or monoclonal antibody corresponding thereto. A detailed exemplification of obtaining polyclonal antibody is set forth in Example IX hereinafter and purification thereof is described in Examples X and XII hereinafter. Monoclonal antibody may be prepared by methods known in the art by forming hybridomas from antibody-secreting lymphocytes and screening for hybridoma producing the desired antibody and utilizing the selected hybridoma for monoclonal antibody production.

As indicated above, the anti L-amino acid oxidase antibody is preferably administered in step (b) in the second embodiment herein at a dosage ranging from about 1 to about 5 µg anti L-amino acid oxidase antibody per unit of L-amino acid oxidase administered in step (a) and the administration of the anti L-amino acid oxidase antibody is preferably carried out from about 1½ to about 6 hours after the administration of step (a).

The anti L-amino acid oxidase antibody can be administered by any parenteral route, e.g., intravenously, intraperitoneally or subcutaneously. A preferred method of administration for human patients is intravenous administration as a bolus injection.

The anti L-amino acid oxidase antibody is appropriately diluted at a level (antibody:diluent) ranging from 100 µg/ml to 30 mg/ml depending on the purity of the antibody, e.g., using normal saline as the diluent.

Preferably, the anti L-amino acid oxidase antibody is administered to inhibit plasma L-amino acid oxidase activity so that the plasma L-amino acid oxidase activity is less than 10% of the plasma L-amino acid oxidase activity one hour after the administration of step (a), this reduction in plasma L-amino acid oxidase activity being caused by the combination of anti L-amino acid oxidase caused inhibition and metabolism of L-amino acid oxidase unrelated to anti L-amino acid oxidase antibody administration.

We turn now to step (c) of the second embodiment.

As indicted above, this step comprises administering large neutral amino acid drug in a therapeutically effective amount to the patient wherein plasma level of large neutral amino acid is reduced from normal level, within about 1 to 10 hours after the administering in step (b) and within about 2 to 36 hours after the administering in step (a), so as to improve the transport of the large neutral amino acid drug across the blood brain barrier, as evidenced by better treatment results with the same dosage of drug as are obtained in the absence of L-amino acid oxidase treatment or the same treatment results with a lesser dosage of drug than are obtained in the absence of L-amino acid oxidase treatment.

As indicated above, the administration of step (c) is preferably carried out from about 1 to 10 hours after the administration of step (b) and about 2½ hours to 20 hours after the administering in step (a).

The dosages and routes of administration for various large neutral amino acid drugs are discussed above.

We turn now to the preferred methods herein where patients with brain tumors are treated where the administration of anti-tumor effective large neutral amino acid drug is preceded by administration of large neutral amino acid glutathione depleting agent which is not metabolized by L-amino acid oxidase, in an amount to make the brain tumors more susceptible to the cytotoxic efforts of the large neutral amino acid drugs. Large neutral amino acid glutathione depleting agents which are not metabolized by L-amino acid oxidase include L-buthionine-SR-sulfoximine, i.e., L-(S-n-butyl)homocysteine-SR-sulfoximine, L-buthionine-S-sulfoximine, S-(3-methyl) butyl homocysteine-SR-sulfoximine, S-(2-methyl)butyl homocysteine-SR-sulfoximine, S-(2-ethyl)butyl homocysteine-SR-sulfoximine, and S-(cyclohexyl)methyl homocysteine-SR-sulfoximine. L-Buthionine-SR-sulfoximine can be prepared as described in Griffith, O. W., The Journal of Biological Chemistry, Vol. 257, No. 22, pp. 13704–13712 (1982). The preparation of L-buthionine-S-sulfoximine is described in Griffith U.S. Pat. No. 5,171,885. The others are described in Anderson, M. E., et al, FASEB J. 2, A1545 (1988) and are readily synthesized by the general methods described in Griffith, O. W., The Journal of Biological Chemistry, Vol. 257, No. 22, pp 13704–13712 (1982). Dosages range from 20 to 80 mg/kg/dose and route of administration is oral or parenteral administration. Administration of the large neutral amino acid glutathione depleting agent is preferably carried out from 3 to 6 hours before administration of the large neutral amino acid drug and from about 1½ to 6 hours after administration of the L-amino acid oxidase. The administration of the glutathione depleting agent 1½ to 6 hours after the administration of L-amino acid oxidase, i.e., when the plasma level of large neutral amino acid is reduced, improves the transport of the glutathione depleting agent across the blood brain barrier into the brain.

We turn now to the method of the third embodiment of the invention herein,, i.e., the embodiment where large neutral amino acid glutathione depleting agent is administered to deplete glutathione in a brain tumor prior to radiation therapy to made the tumor more susceptible to radiation therapy and L-amino acid oxidase is administered prior to the administration of the large neutral amino acid glutathione depleting agent to improve the transport of the large neutral amino acid glutathione depleting agent across the blood brain barrier. As indicated, the tumors treated are those susceptible to radiation therapy and include the brain tumors mentioned above in the paragraph about "brain associated disease." The administration of large neutral amino acid glutathione depleting agents as an adjunct to radiation therapy in the treatment of brain tumors is described in Lippitz, B. E., et al., Neurosurgery 26, 255–260 (1990) and in Halperin, E. C., et al., Int. J. Radiation Oncology Biol. Phys., 24, 103–109 (1992) and the disclosure of these articles is incorporated herein by reference. The L-amino acid oxidase is administered in a dosage ranging from about 1 to about 100 units/ml of plasma (corresponding to about 85 to about 8,500 units/kg of body weight) which is non-toxic and what is sufficient to reduce plasma level of large neutral amino acids from a normal level to a large neutral amino acid glutathione depleting agent transport improving level and the large neutral amino acid glutathione depleting agent is one which is not metabolized by L-amino acid oxidase and is administered to patient wherein plasma level of large neutral amino acids is reduced from normal level and about 1½ to 6 hours after the administration of the L-amino acid oxidase in an amount ranging from 20 to 80 mg/kg and this administration is carried out on a daily basis and continued for as many days as is necessary to deplete glutathione in the tumor that is to be irradiated to make the tumor more susceptible to the radiation treatment. Examples of dosage ranges for the L-amino acid oxidase within the range of about 1 to 100 units/ml of plasma are the same as those described above. The L-amino acid oxidase can be administered by any parenteral route and is preferably administered intravenously. The large neutral amino acid glutathione depleting agents are exemplified above and the route of administration is oral or parenteral. The number of days of administration of the combination to deplete glutathione in the tumor can range, for example, from 1 to 10 days. The radiation therapy may be that conventionally utilized for treatment of the brain tumor being irradiated. Radiation therapy can comprise, for example total doses ranging from 5400 to 6600 cGy at the prescription point administered at 120 to 180 cGy/day. Interstitial radiation as described in said Lippitz et al. article can be utilized.

As indicated in Pardridge, W. M., et al., Fed. Proc. 45, 2073–2078 (1986), the uptake of large neutral amino acids is not controlled by the neutral amino acid transporter in most tissues but is controlled by that transporter at the blood brain barrier because only at the blood brain barrier is the $K_m$ for each of the large neutral amino acids low enough to allow inhibition. This means that reducing plasma level of large neutral amino acids will increase uptake of large neutral amino acid drug and/or large neutral amino acid glutathione depleting agent into brain but will not alter the uptake of large neutral amino acid drug into peripheral tissues.

Both embodiments of the invention are illustrated in examples which follow.

D-54MG gliomas are utilized in Examples VI, VII, XIII, and XIV. D-54MG was chosen as the tumor model for the experiments, not because of any specific relevance of glioma as opposed to any other histology, but rather because from a technical standpoint, D-54 MG was an excellent choice. This is because said studies require a tumor that would grow within a precise parenchymal focus in the brain and not spread beyond the site of injection and D-54 MG meets this criterion since it had been shown to stay confined to the area of injection and never to involve the contralateral hemisphere. This enables evaluation of the modulation of melphalan delivery to normal brain as well as to tumor in brain. D-54 MG was chosen for subcutaneous studies concomitant with the intracranial studies to enable differentiation of increased delivery to intracranial tumors secondary to increased delivery to the brain versus increased passage across the tumor cell membranes. Again there was no reason to focus on glioma. Rather D-54 MG grows in a very convenient fashion for both intracranial and subcutaneous studies.

EXAMPLE I

The kinetic constants $K_m$, $V_{max}$ and $(V_{max})/(Km)$ for L-amino acid oxidase with various amino acid substrates were determined, where $K_m$ stands for the concentration in mM of substrate required for reaction at a rate of 0.5 $V_{max}$ and $V_{max}$ is the maximum rate of product formation achieved per mg of L-amino oxidase as the concentration of substrate approaches infinity, and $(V_{max})/(Km)$ is the best measure of L-amino acid oxidase activity toward a substrate. $K_m$ and $V_{max}$ were determined by plotting 1/rate vs. 1/[substrate] to give a line which intersects the Y-axis at $1/V_{max}$ and intersects the X-axis at $-1/K_m$. The reaction mixtures utilized contained in a final volume of 1.0 ml, the following: 100 mM glycylglycine buffer, pH 7.5, 0.3 mM NADH, 2 mM α-ketoglutarate, 0.5 mM ADP, 20 I.U. glutamate dehydrogenase (Sigma Chemicals, St. Louis, Mo.), and L-amino acid substrate or melphalan at concentrations ranging from 0.1 to 16 mM. The temperature was 37° C. In this system L-amino acid oxidase converted L-amino acid or melphalan to the corresponding α-keto acid and ammonia; ammonia then reacted stoichiometrically with α-ketoglutarate and NADH in a reaction catalyzed by glutamate dehydrogenase to give $NADH^+$ and glutamate. The oxidation of NADH to $NAD^+$ is accompanied by a decrease in $OD_{340}$, which was monitored and used to determine the amount of ammonia made available for reaction (1 mM NADH converted to $NAD^+$ causes a $\Delta OD_{340}$ of 6.2 in the 1 cm cuvettes used).

The data is set forth in Table 1 below:

| Substrate | $K_m$ (mM) | $V_{max}$ (μmol/min · mg) | $(V_{max})/(K_m)$ |
|---|---|---|---|
| L-Alanine | N/A | 0 | 0 |
| L-Leucine | 0.6 | 100 | 167 |
| L-Isoleucine | 2.05 | 33 | 16 |
| L-Valine | 19 | 13 | 0.7 |
| L-Methionine | 0.47 | 70 | 150 |
| L-Phenylalanine | 0.13 | 33 | 261 |

-continued

| Substrate | $K_{m\ (mM)}$ | $V_{max}$ (µmol/min · mg) | $(V_{max})/(K_m)$ |
|---|---|---|---|
| L-Tryptophan | 0.22 | 43 | 194 |
| L-Tyrosine | 0.13 | 37 | 295 |
| Melphalan | 0.30 | 11 | 37 |

The data provides a screening test indicating that L-amino acid oxidase has potential in vivo for reducing the level of the large neutral amino acids L-leucine, L-methionine, L-phenylalanine, L-tryptophan and L-tyrosine without unduly degrading melphalan or other large neutral amino acid drugs.

EXAMPLE II

Mice (20–25 gm) were administered either 300 µg or 200 µg of pure L-amino acid oxidase by intravenous injection. At 12, 18, 24 and 36 hours after administration, the L-amino acid oxidase activity of the plasma was determined.

L-Amino acid oxidase activity was determined as follows: Blood was obtained from the heart in a heparinized syringe. After centrifugation (10,000×g) for 30 seconds, plasma was obtained as the supernatant. Then assay reaction mixtures were made up (100 µl final volume) containing 400 mM Tris HCl buffer, pH 7.5, 1 mM L-[$^{14}$C]leucine (0.08 µCi) and 40 µl plasma. The reaction mixtures were incubated for 10 min. at 37° C. The reaction was stopped by addition of 100 µl of 20% trichloroacetic acid and the vials were placed on ice for five min. The reaction mixtures were then centrifuged for 1 min. to sediment precipitated protein, and 180 µl of supernatant was loaded onto a small column (0.5×2.5 cm) of Dowex 50W× 8 (200–400 mesh) cation exchange resin (H$^+$-form). The columns were washed with 3.8 ml of water, and the effluent which contains α-keto-[$^{14}$C]isocaproic acid, the product of L-amino acid oxidase activity on leucine, was collected in a test tube and mixed. Radioactivity in two ml of the mixed effluent was determined by liquid scintillation counting. The amount of product formed (nmol/min) is determined from the known specific activity of the L-[$^{14}$C] leucine used. The amount of L-amino acid oxidase is calculated by knowing that 1 mg of enzyme forms 100 nmol product/min under these conditions.

Since mice of the size used have about 2 ml of blood and 1.2 ml of plasma, the peak plasma concentration of L-amino acid oxidase is calculated to be about 250 and 167 µg/ml in the mice given 300 and 200 µg of L-amino acid oxidase, respectively. These peak concentrations would occur immediately following injection.

The results as determined at 12, 18, 24 and 36 hours are shown in FIG. 1 wherein the open circles denote results on administration of 200 µg of L-amino acid oxidase and the filled in squares denote results on administration of 300 µg of L-amino acid oxidase. The graphs are defined by points representing the mean ±S. D. for data for 3 mice. As indicated in FIG. 1, L-amino acid oxidase activity in plasma decreases with time after 12 hr. but persists for at least 24 hours. By 36 hr., activity was essentially zero.

Plasma large neutral amino acids were determined at the 12, 18 and 24 hours after L-amino acid oxidase administration.

Results for 300 µg intraperitoneal administration of L-amino acid oxidase are set forth in Table 2 below wherein "control" is the amino acid level in mice where L-amino acid oxidase was not administered. Concentrations are given as µM.

TABLE 2

| Amino Acid | Control | 6 hr | 24 hr | 36 hr | 48 hr |
|---|---|---|---|---|---|
| Leucine | 222 | 121 | 168 | 234 | 180 |
| Methionine | 97 | 56 | 67 | 106 | 106 |
| Phenylalanine | 95 | 62 | 46 | 78 | 70 |
| Tryptophan | 70 | 54 | 48 | 62 | 92 |
| Tyrosine | 133 | 71 | 42 | 63 | 87 |

The above data suggests that plasma large neutral amino acids can be efficiently depleted by the injected dose between 6 and 24 hr after administration. In the period from 24 to 36 hours, the remaining activity is adequate to maintain plasma levels of some large neutral amino acids at a low level. The dose used is not so high that melphalan or other large neutral amino acid drug would be degraded rapidly.

EXAMPLE III

Mice (20–30 gm) were administered either 100 µg, 200 µg, 300 µg or 400 µg of L-amino acid oxidase by intravenous injection.

Figure 2:
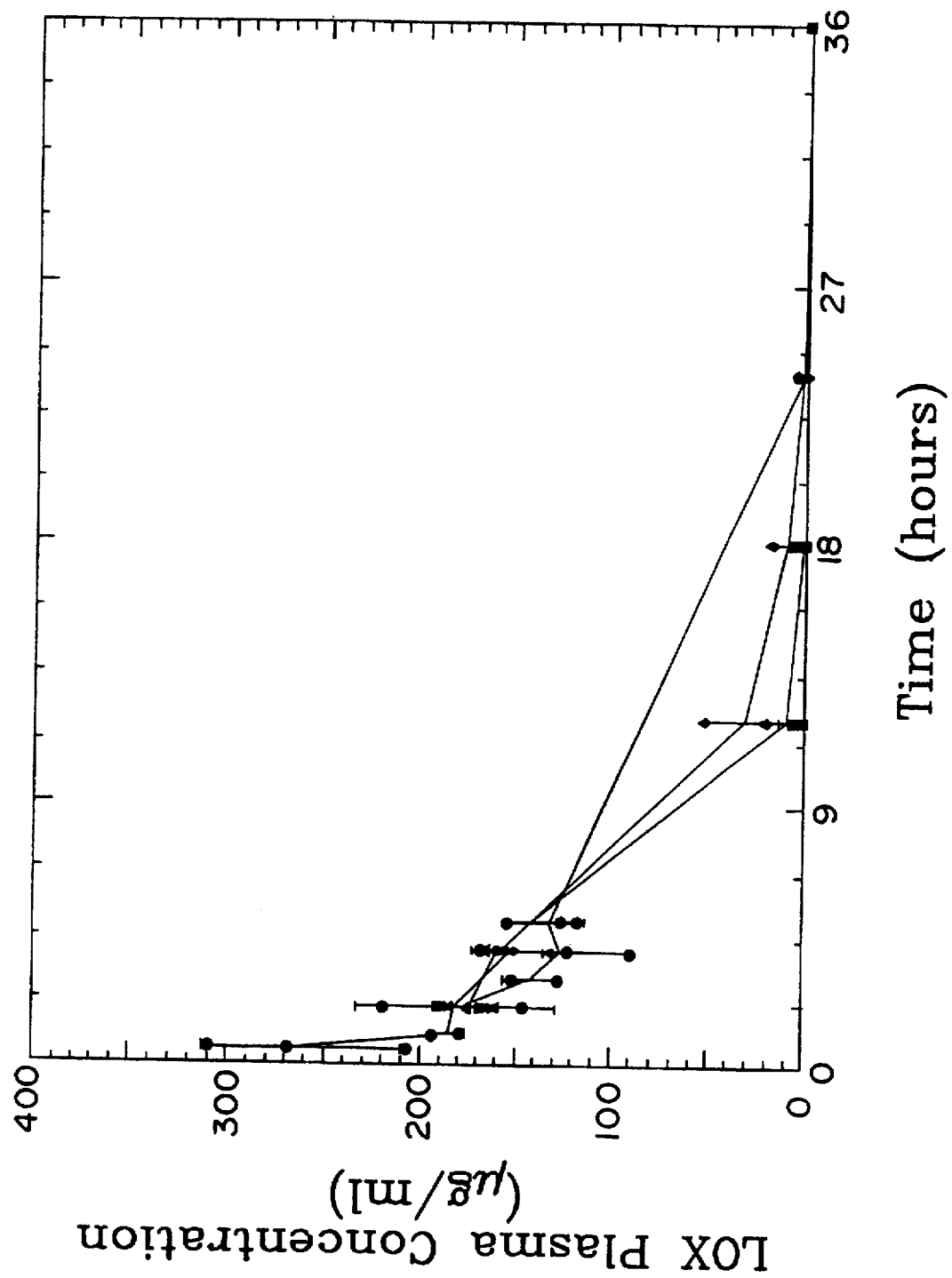
FIG. 2 depicts graphs of L-amino acid oxidase plasma concentration (denoted "Plasma LOX concentration") vs. time after intravenous treatment of mice with various doses of L-amino acid oxidase, showing plasma L-amino oxidase activity at denoted intervals after L-amino acid oxidase treatment, based on data determined in Example III.

Plasma L-amino oxidase activity was determined at intervals thereafter as shown in FIG. 2 wherein the circles denote results on administration of 100 µg, the squares denote results on administration of 200 µg, the diamonds denote results on administration of 300 µg, and the triangles denote results on administration of 400 µg.

The graphs are defined by points representing the mean ±S. D. for 3 mice.

As shown in FIG. 2, the plasma L-amino oxidase concentration was greater than 50 µg/ml at all times up to 9 hours.

The large neutral amino acid levels corresponding to the L-amino oxidase levels of FIG. 2 are given in Table 3 below:

TABLE 3

| Time (hr) | Dose (units) | Plasma Amino Acids | | | | |
|---|---|---|---|---|---|---|
| | | Leucine (µM) | Isoleucine (µm) | Methionine (µM) | Phenylalanine (µM) | Tyrosine (µM) |
| 0 | — | 244 ± 73 | 150 ± 42 | 125 ± 39 | 144 ± 40 | 165 ± 64 |
| 0.5 | 2 | 42 ± 6 | 103 ± 7 | 28 ± 3 | 10 ± 0 | 5 ± 0 |
| 1 | 2 | 75 ± 22 | 110 ± 11 | 42 ± 16 | 13 ± 9 | 7 ± 3 |
| 2 | 2 | 26 ± 6 | 86 ± 3 | 22 ± 4 | 5 ± 0 | 5 ± 0 |
| 3 | 2 | 101 ± 62 | 125 ± 26 | 38 ± 20 | 22 ± 25 | 13 ± 13 |
| 4 | 2 | 148 ± 21 | 144 ± 9 | 65 ± 17 | 40 ± 11 | 27 ± 6 |
| 5 | 2 | 51 ± 26 | 100 ± 26 | 22 ± 5 | 8 ± 3 | 5 ± 0 |

TABLE 3-continued

| Time (hr) | Dose (units) | Plasma Amino Acids | | | | |
|---|---|---|---|---|---|---|
| | | Leucine (μM) | Isoleucine (μm) | Methionine (μM) | Phenylalanine (μM) | Tyrosine (μM) |
| 24 | 2 | 253 ± 16 | 165 ± 4 | 108 ± 12 | 112 ± 25 | 90 ± 33 |
| 2 | 4 | 13 ± 11 | 86 ± 18 | 28 ± 14 | 5 ± 0 | 5 ± 0 |
| 4 | 4 | 23 ± 9 | 98 ± 12 | 18 ± 1 | 5 ± 0 | 5 ± 0 |
| 12 | 4 | 152 ± 52 | 90 ± 30 | 76 ± 18 | 55 ± 16 | 64 ± 41 |
| 18 | 4 | 165 ± 13 | 96 ± 10 | 80 ± 11 | 60 ± 3 | 46 ± 2 |
| 24 | 4 | 159 ± 41 | 93 ± 22 | 66 ± 19 | 65 ± 13 | 53 ± 11 |
| 36 | 4 | 151 ± 11 | 83 ± 10 | 49 ± 1 | 63 ± 2 | 55 ± 3 |
| 2 | 6 | 5 ± 0 | 45 ± 6 | 18 ± 1 | 5 ± 0 | 5 ± 0 |
| 4 | 6 | 5 ± 0 | 51 ± 14 | 16 ± 3 | 5 ± 0 | 5 ± 0 |
| 12 | 6 | 153 ± 32 | 95 ± 27 | 72 ± 14 | 55 ± 6 | 48 ± 8 |
| 18 | 6 | 157 ± 14 | 97 ± 6 | 81 ± 13 | 51 ± 5 | 37 ± 8 |
| 24 | 6 | 101 ± 26 | 61 ± 13 | 54 ± 13 | 46 ± 12 | 40 ± 5 |
| 36 | 6 | 164 ± 44 | 88 ± 20 | 58 ± 20 | 65 ± 7 | 78 ± 40 |
| 2 | 8 | 5 ± 0 | 42 ± 8 | 13 ± 5 | 5 ± 0 | 5 ± 0 |
| 4 | 8 | 5 ± 0 | 56 ± 17 | 14 ± 3 | 5 ± 0 | 5 ± 0 |

As indicated in Table 3, the concentration of large neutral amino acids during 30 minutes to 5 hours after administration is reduced to a very low level thereby providing high melphalan transfer constants for plasma to tumor tissue transfer. While melphalan administered in the first 6 hours following L-amino acid oxidase administration will be partially degraded by the high levels of L-amino acid oxidase present, in some cases the L-amino acid oxidase mediated decrease in plasma amino acids can cause an increase in tumor uptake of melphalan that more than compensates for the L-amino acid oxidase mediated partial degradation of melphalan.

EXAMPLE IV

Melphalan was allowed to react with L-amino acid oxidase in a reaction mixture (final volume, 100 μl ) containing phosphate buffered saline, pH 7.4, 50 μM [$^{14}$C]melphalan and 125 μg/ml (12.5 units/ml) L-amino acid oxidase. At 5, 15 and 30 minutes after formation of the reaction mixture, 10 μl aliquots were removed and fractionated by HPLC.

The HPLC was carried out on a BROWNLEE C18 reverse phase column under the following conditions: Solvent, 0.1 M ammonium acetate, pH 4.1, with 79% methanol; flow rate 1 ml/min for 15 min, then 1.5 ml/min; fractions of 1 min collected and radioactivity determined by liquid scintillation counting.

The HPLC eluant was analyzed for radioactivity and peaks associated with melphalan (elution time, 8–9 min), or its reaction products (products I and II eluting at 10–12 and 23.5–25 min, respectively) were determined. The control incubation contained no L-amino acid oxidase, but was analyzed similarly. Product I is believed to be ketomelphalan, i.e., 4-[bis(2-chloroethyl)amino] phenylacetate.

Figure 3:
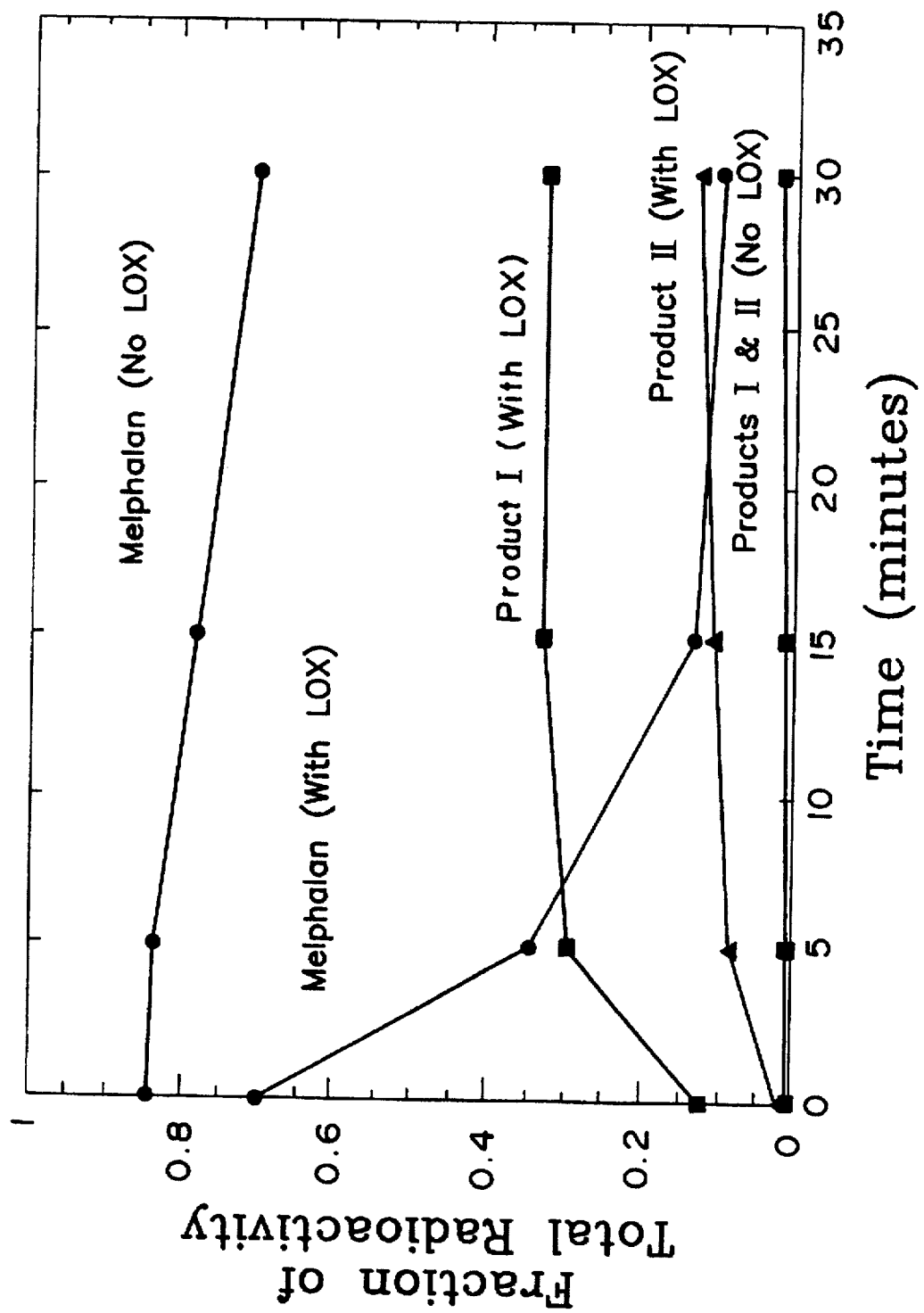
FIG. 3 depicts graphs of fraction of total radioactivity versus time, based on data determined in Example IV directed to HPLC determination of melphalan (50 µM) reaction with L-amino acid oxidase (0.25 mg/ml) and a control with no L-amino acid oxidase.

The results are shown in FIG. 3 wherein LOX stands for L-amino acid oxidase.

As shown in FIG. 3., melphalan showed good stability for at least 30 minutes in the absence of L-amino oxidase and in the presence of L-amino acid oxidase at 12.5 units/ml was degraded at an initial rate of 50% reaction in 5 minutes.

In this concentration range, the rate of L-amino acid oxidase mediated melphalan degradation is expected to be essentially directly proportional to the L-amino acid oxidase concentration. Thus, at a plasma L-amino acid oxidase concentration of 1.25 units/ml, melphalan is expected to be degraded with a period required for 50% reaction of 50 minutes, and at a plasma concentration of 0.25 units/ml, melphalan is expected to be degraded with a period required for 50% reaction of 250 minutes. As shown in FIG. 1, L-amino acid oxidase concentrations are 1.25 units/ml (12.5 μg/ml) or less 12 to 15 hours following 200 to 300 μg L-amino acid oxidase administration. In particular, as indicated from FIG. 1, melphalan is expected to be degraded with a period required for 50% reaction ranging from 50 to 250 minutes when administered 12 to about 30 hours after L-amino acid oxidase administration at the concentrations of L-amino acid oxidase administered in Example II. Studies in man have indicated that the disappearance of most melphalan from plasma is 50% complete after 7.7 minutes. This uptake would be expected to be increased with the plasma large neutral amino acid reduction provided by L-amino acid oxidase. Thus uptake of melphalan into brain tumors would be more than 50% complete, 75% complete and 87.5% complete 7.7 min, 15.4 min and 23.1 min following injection, i.e. within the period indicated for 50% melphalan reaction.

The above provides a rational basis for estimating the appropriate time following L-amino acid oxidase administration, to administer melphalan. Each tumor type will have its characteristic affinity for melphalan. Thus for a tumor type where uptake is relatively fast (50% uptake in 30 minutes or less), uptake will be greater than 87% complete in 90 minutes. At a plasma concentration of 5 μg/ml (melphalan administration about 18 hrs after 167 μg/ml L-amino oxidase injection or about 30 hrs after 250 μg/ml injection), less than 25% of the melphalan would be metabolized by the L-amino acid oxidase in 90 minutes (time required for 50% reaction of 250 min, k=0.00276 min) in the absence of melphalan uptake. Considering that melphalan was taken up into tumors simultaneously with L-amino acid oxidase mediated metabolism, the loss of melphalan is expected to be less than 10%. Since L-amino acid oxidase mediated removal of plasma large neutral amino acids will improve melphalan uptake by more than 10%, the small loss of melphalan due to L-amino acid oxidase mediated metabolism can be considered insignificant provided the L-amino acid oxidase dose and timing of the melphalan injection are properly adjusted.

EXAMPLE V

Mice (20–25 gm) were given melphalan and/or L-amino acid oxidase by intraperitoneal injection. Melphalan was administered at 1.0 or 0.5 times the previously established $LD_{10}$ dose (dose where 10% die), namely 11.8 and 23.7 μmole/kg body weight, respectively. Highly purified L-amino oxidase was given at a dose of 100 μg or 400 μg per mouse in two separate experiments. Results for the first experiment are shown in the first 5 entries in Table 4 below. Results for the second experiment are shown in the last three entries in Table 4 below. In Table 4 below, "LOX" means L-amino acid oxidase.

TABLE 4

| Treatment | Mean Nadir weight loss (g) | Mean Nadir Percentage Weight Loss (%) | Deaths |
|---|---|---|---|
| 1.0 $LD_{10}$ Melphalan | 9.2 | 31.8 | 0/6 |
| 0.5 $LD_{10}$ Melphalan | 4.2 | 16.6 | 0/6 |
| 100 μg LOX | 0.3 | 1.1 | 0/6 |
| 100 μg LOX & 1.0 $LD_{10}$ Melphalan | 5.8 | 19.8 | 0/6 |
| 100 μg LOX & 0.5 $LD_{10}$ Melphalan | 4.7 | 16.3 | 0/6 |
| 1.0 $LD_{10}$ Melphalan | 4.3 | 14.6 | 0/6 |
| 400 μg LOX | 0.0 | 0.0 | 0/6 |
| 400 μg LOX & 1.0 $LD_{10}$ Melphalan | 3.0 | 12.5 | 2/6 |

As shown in Table 4, melphalan alone at either dose caused significant weight loss but no deaths in 6 mice; L-amino acid oxidase alone at either dose caused no deaths and no significant weight loss in the mice; at the lower dose of L-amino acid oxidase, melphalan plus L-amino acid oxidase caused significant weight loss but no deaths in 6 mice; at the highest doses, melphalan plus L-amino acid oxidase resulted in the death of 2 of 6 mice but weight loss was not greater than with melphalan alone. Overall, the results indicate that L-amino acid oxidase does not significantly increase the toxicity of melphalan at 1.0 or 0.5 times its $LD_{10}$ dose. The difference between the results for "1.0 $LD_{10}$ Melphalan" in the two experiments in Table 4 may be explained by the biological variability which is always seen in these types of experiments.

EXAMPLE VI

Subcutaneous D-54 MG tumors (a human glioma-derived continuous cell line), grown in athymic BALB/C mice were excised and mechanically homogenized in zinc option medium as described in Bullard, D. E., J. Neuropath. Exp. Neurol. 40:410–427, 1981. The homogenate was mixed with an equal amount of 1% methylcellulose and 10 μl of homogenate (about $10^5$ tumor cells) injected into the right frontal hemisphere of athymic mice (20–25 gm) for brain, i.e., intracranial (IC) tumors and 50 μl of homogenate was injected subcutaneously into the right flank for subcutaneous (SC) tumors.

The effects on tumor growth and animal survival of melphalan and L-amino acid oxidase, alone and in combination, were determined in groups of mice previously injected intracranially or subcutaneously with tumor cell line as described above.

L-amino acid oxidase was administered at a dose of 100 μg (83 μg/ml in plasma) or a dose of 400 μg (333 μg/ml in plasma) by intravenous injection 8 days after injection of tumor cells. Melphalan when used alone was administered at a dose of 0.5 times or 1.0 times its LD10 dose by intraperitoneal injection 8 days after injection of tumor cells. Melphalan when used in combination with L-amino acid oxidase was administered intraperitoneally 2 hours after L-amino acid oxidase injection.

The results are shown in Table 5 below wherein LOX means "L-amino acid oxidase", MDTD means "mean days to death", T-C means growth delay to 5 times pretreatment volume for treated tumors minus growth delay to 5 times pretreatment volume for untreated tumors and regressions means percentage of mice where tumors became smaller.

TABLE 5

| | Intracranial D54 MG | | Subcutaneous D54 MG | |
|---|---|---|---|---|
| Treatment | MDTD | Long Term Survivors | T-C | Regressions (%) |
| No Treatment | 19.5 | 0/10 | 0 | 0/10 (0%) |
| LOX (100 μg i.v.) | 22.0 | 0/10 | 0.2 | 0/10 (0%) |
| Melphalan (0.5 $LD_{10}$) | 26.5 | 0/10 | 7.2 | 2/10 (20%) |
| Melphalan (0.5 $LD_{10}$) & LOX (100 μg i.v.) | 27.0 | 0/10 | 8.9 | 5/10 (50%) |
| Melphalan (1.0 $LD_{10}$) | 34.0 | 0/10 | 13.3 | 6/10 (50%) |
| Melphalan (1.0 $LD_{10}$) & LOX (100 μg i.v.) | 33.0 | 0/10 | 14.6 | 5/8 (63%) |

As shown in Table 5, L-amino acid oxidase (LOX) alone had little effect on the growth of either intracranial (IC) or subcutaneous (SC) tumors. Melphalan alone at a dose of 0.5 times the $LD_{10}$ dose caused a 7.0 day increase in median survival time of mice with intracranial tumors compared to untreated control and a 7.2 day growth delay to 5 times pretreatment volume with two regressions in 10 mice with subcutaneous tumors. Administration of L-amino acid oxidase with this dose of melphalan increased median survival time to 7.5 days over untreated control for intracranial tumors and increased the growth delay to 5 times pretreatment volume to 8.9 days, with 5 regressions in 10 mice. At a higher dose of melphalan (1.0 times the $LD_{10}$ dose), the administration of L-amino acid oxidase did not improve the response of intracranial tumors but did improve the response of subcutaneous tumors.

EXAMPLE VII

Intracranial (IC) D-54 MG tumors were grown in Balb/C mice as described in Example VI. Treatment groups were None (Control), Melphalan alone, Melphalan +diet, Melphalan +LOX, and Melphalan+diet+LOX ("LOX" is used to mean L-amino acid oxidase). L-amino acid oxidase was administered intravenously at a dose of 300 μg per mouse. Melphalan was administered intraperitoneally at a dose of 1.0 times its $LD_{10}$ (the dose previously determined to kill 10% of the animals when used alone). Animals were carefully monitored to determine "days to death." Scheduling for the treatment groups was as follows: Mice in the "None (Control)" group received no treatment and the "days to death", therefore, represent survival in days after implantation of the intercranial tumors. Animals in the "Melphalan alone" group received melphalan 6 days after tumor implantation and the "days to death" values indicate days of survival after tumor implantation. Animals in the "Melphalan +diet" group were fasted for 18 hours beginning 5 days after tumor implantation and were then allowed free access to a protein-free diet (Bio-Serv Inc. catalogue #F2247) for 6 hours after the fast; at that time melphalan was administered, and the animals were allowed a further 2 hours access to the protein-free diet. Animals were then returned to cages with conventional diet and were monitored for survival; "days to death" indicates survival in days following tumor implantation. Animals in the "Melphalan +LOX" group received 300 μg of L-amino acid oxidase 5 days after tumor implantation and 24 hours after L-amino acid oxidase administration were given melphalan. "Days to death" indicates survival in days after tumor implantation. Animals in the "Melphalan+diet+LOX" group received 300 µg of L-amino acid oxidase 5 days after tumor implantation and were fasted for 18 hours after L-amino acid oxidase administration. Animals were then allowed access to a protein-free diet (Bio-Serv Inc. Catalogue #F2247) for 6 hours and were injected with melphalan 24 hours after L-amino acid oxidase administration. Access to the protein-free diet was continued for 2 hours after melphalan administration, and the animals were then returned to cages with conventional diet (standard rodent chow) and were monitored for survival. Results are set forth in Table 6 below wherein "Days to Death" indicates survival in days after tumor implantation.

TABLE 6

| Treatment | Days to Death | Median Days to Death | Number of Mice Surviving Beyond Control Range |
|---|---|---|---|
| None (Control) | 19, 19, 21, 23, 24, 24 25, 27, 29, 29 | 24 | |
| Melphalan alone | 20, 20, 27, 27, 36, 36 41, 41, 42, 42 | 36 | 6 |
| Melphalan + diet | 17, 20, 23, 26, 33, 36 37, 42, 46, 47 | 34 | 6 |
| Melphalan + LOX | 19, 21, 22, 30, 30, 30 30, 33, 36, 38 | 30 | 7 |
| Melphalan + diet + LOX | 19, 19, 19, 36, 36, 44 44, 44, 46, 47 | 40 | 7 |

The results shown in Table 6 indicate that tumor bearing animals receiving no treatment died between 19 and 29 days following tumor implantation with a mean survival of 24 days. Melphalan alone increased survival in some but not all animals; mean survival increased to 36 days. Six of the 10 treated animals had survival times greater than any of the animals receiving no treatment. Some but not all animals receiving melphalan after fasting and exposure to a protein-free diet showed increased survival relative to animals receiving no treatment; mean survival was 34 days. Six of the 10 animals in this group had survival times greater than any of the animals receiving no treatment. Two of the animals had survival times exceeding those observed in the group of animals receiving melphalan alone. Some but not all animals receiving melphalan+L-amino acid oxidase exhibited survival times greater than the range of survival times observed in the animals receiving no treatment; mean survival was 30 days. Seven of 10 animals in this group had survival times greater than any of the animals receiving no treatment. Some but not all animals in the group receiving L-amino acid oxidase and given melphalan after a fast and protein-free diet exhibited survival times greater than those observed in the group receiving no treatment. Mean survival time was 40 days; a value greater than that observed with any other treatment group. Seven of the 10 animals exhibited survival times greater than any of the animals receiving no treatment. Five of the 10 animals exhibited survival times greater than any observed in the group receiving melphalan alone. Median survival time in the group receiving melphalan+dietary manipulation+L-amino acid oxidase was greater than median survival time in the group receiving melphalan+dietary manipulation alone.

EXAMPLE VIII

Groups consisting of three BALB/C athymic mice (20 to 25 gm) received an average dose of either 100 µg L-amino acid oxidase or 200 µg L-amino acid oxidase intravenously through tail vein injection at t=0 hours. Mice were serially eyebled with a heparinized microtiter pipette at timepoints equal to 0, 1, 2, 3, 4, 6 and 8 hours after L-amino acid oxidase injection. Mice received a 1 ml bolus of normal saline subcutaneously to the neck scruff at t=1.5 hours post L-amino acid oxidase injection to obtain 40 µl blood samples. Each 40 µl blood sample was spun at 7000 rpm for 10 minutes. In each case, 20 µl plasma was removed and transferred to an Ependorf tube containing 80 µl (5%) 5-sulfosalicylic acid. After spinning for 10 minutes, the samples were stored at −80° C. Samples were shipped on Dry Ice to the Medical College of Wisconsin where plasma levels of the large neutral amino acids histidine, isoleucine, leucine, methionine, phenylalanine, tyrosine and valine were measured on a Beckman analyzer. At doses averaging 100 µg L-amino acid oxidase, maximum depletions achieved were: 34.6% histidine (t=3 hours); 59.89% isoleucine (t=3 hours); 66.4% leucine (t=3 hours); 80.15% methionine (t=3 hours); 89.89% phenylalanine (t=3 hours); 95.67% tyrosine (t=3 hours); and 44.13% valine (t=3 hours). At doses averaging 200 µg L-amino acid oxidase, maximum depletions achieved were: 17.62% histidine (t=3 hours); 53.28% isoleucine (t=3 hours); 64.56% leucine (t=3 hours); 85.25% methionine (t=8 hours); 86.43% phenylalanine (t=8 hours); 94.81% tyrosine (t=8 hours); and 53.1% valine (t=3 hours).

EXAMPLE IX

BALB/C mice were injected subcutaneously with 50 µg L-amino acid oxidase in complete Freund's adjuvant, 0.2 ml/mouse and bled on days 16 and 41 post primary immunization. Four SPR rabbits (#899, 2876, 2877, 2878) were injected subcutaneously with 500 µg L-amino acid oxidase in 0.5 ml saline and 0.5 ml complete Freund's adjuvant. Rabbits were bled on days 22 and 36 post primary immunization. Rabbits were boosted with 500 µg L-amino acid oxidase in 0.5 ml saline and 0.5 ml complete Freund's adjuvant, 53 days after primary immunization and bled on days 40 and 79 post secondary immunization. Third immunization with 500 µg L-amino acid oxidase in 0.5 ml saline and 0.5 ml complete Freund's adjuvant occurred 102 days after secondary immunization and rabbits were bled on days 7 and 14 post third immunization. Rabbit #2877 was sacrificed after first bleed post secondary immunization due to loss of blood supply to foot. Goat #348 was immunized with 500 µg L-amino acid oxidase in 1.0 ml saline and 1.0 ml complete Freund's adjuvant divided and injected subcutaneously at four sites. Goat was bled on day 36 post primary immunization. Secondary immunization with 500 µg L-amino acid oxidase in 1.0 ml saline and 1.0 ml complete Freund's adjuvant injected subcutaneously at four sites took place 60 days after primary immunization and goat was bled on days 48, 85 and 90 post secondary immunization. Third immunization with 500 µg L-amino acid oxidase in 1.0 ml saline and 1.0 ml complete Freund's adjuvant injected subcutaneously at four sites took place on day 93 post secondary immunization. Goat #348 was bled on day 31 post third immunization.

Immunoglobulin titers were determined by enzyme-linked immunosorbent (ELISA) method. L-Amino acid oxidase was diluted to a concentration of 1 µg/µl in (0.1M) $Na_2CO_3$ (pH 9.6). Each well of a 96-well plate was coated with 50 µl of the L-amino acid oxidase at 1 µg/µl and the plate incubated overnight at 4° C. The plate was then rinsed five times with a (115 mM) phosphate buffer containing 0.05% BRIJ 35 and 0.05% gelatin. The plate was blocked with the same buffer for 10 minutes at room temperature.

Antiserum was serially diluted and 50 μl of each dilution were applied in triplicate to an L-amino acid oxidase-coated well and allowed to incubate for one hour. The plate was again rinsed five times with a (115 mM) phosphate buffer containing 0.05% BRIJ 35 and 0.05% gelatin. 50 μl of a secondary antibody (biotinylated donkey anti-goat, goat anti-mouse or goat anti-rabbit) were applied to each well and allowed to incubate for one hour. The plate was again rinsed five times with a (115 mM) phosphate buffer containing 0.05% BRIJ 35 and 0.05% gelatin. 50 μl of streptavin-alkaline phosphatase was applied to each well and allowed to incubate for one hour before rinsing five more times. Plates were rinsed twice and color developed by the addition of 100 μl substrate per well. Substrate consisted of 10% diethanolamine buffer (pH 9.6) with (5 mM) $MgCl_2$ and 4 μg/ml paranitrophenylphosphate (pNPP). Absorbance was read with a Flow Laboratories ELISA plate reader, Model MCC/340 at 405 nm. ELISA titration was calculated.

Dilutions were carried out on mouse anti L-amino acid oxidase antisera at levels of 1:25, 1:50, 1:100, 1:200, 1:400, 1:800 and 1:1600. Dilutions were carried out on rabbit anti L-amino acid oxidase antisera at levels of 1:25, 1:50, 1:100, 1:200, 1:400, 1:800 and 1:1600. Dilutions were carried out on goat anti L-amino acid oxidase antisera at levels of 1:25, 1:50, 1:100, 1:200 and 1:400. Dilutions were made utilizing 20 mM Tris, 0.15 M NaCl and 10 mM aminotriazole buffer (pH 7.4) containing 0.05% bovine serum albumen.

Admixtures were made to assess L-amino acid oxidase inhibition by the diluted samples by adding each diluted sample to 30 ng L-amino acid oxidase dissolved in 100 μl of 20 mM Tris, 0.15M NaCl and 10 mM aminotriazole buffer (pH 7.4) containing 0.05% bovine serum albumen.

Assay for L-amino acid oxidase inhibition was carried out by $H_2O_2$ PeroXOquant(Trademark) assay as follows: L-Amino acid oxidase activity was measured as a function of the hydrogen peroxide produced in the conversion of large neutral amino acids to their respective keto acids. All reagents were purchased from Sigma, unless otherwise noted. Each well of a 96-well plate contained a 200 μl reaction mixture, consisting of 50 μl (4 mM) 1-leucine, 50 μl plasma sample with L-amino acid oxidase, and 100 μl of anti L-amino acid oxidase serum diluted in a 20 mM Tris NaCl buffer (pH 7.4) containing (p.0.05%) bovine serum albumin and (10 mM) aminotriazole. Each plate was incubated in a humidity chamber for one hour at 37° C. 25 μl of each reaction mixture was then transferred to another 96-well plate and combined with 200 μl Pierce PeroXOquant(Trademark) reagent. (Pierce PeroXOquant (Trademark) quantitative peroxidase assay kit, lipid compatible formula, Pierce Chemical Company—catalogue #23285). After a 12–15 minute incubation at room temperature, absorbance was read in a Flow laboratories ELISA plate reader, Model MCC/340 at 620 nm. L-Amino acid oxidase activity and percent inhibition were calculated. A $H_2O_2$ standard curve was defined and absorbance measured on the ELISA plate reader so that each plasma sample could be translated into moles of $H_2O_2$ produced per hour and thus, moles of L-amino acid oxidase activity. 50 μl aliquots of $H_2O_2$ dilutions (range 1 mM to 1 m) were combined in the above reaction mixtures in place of the plasma samples of L-amino acid oxidase. Because $H_2O_2$ concentration varies with time, absorbance reading was divided by the $H_2O_2$ extinction coefficient of 43.6 $M^{-1}cm^{-1}$ in order to standardize the concentration of $H_2O_2$ stock.

Raw sera from mouse (post primary immunization), rabbit (post third immunization) and goat (post second immunization) demonstrated maximal L-amino acid oxidase inhibitions of 51.88%, 62% and 28.78% when antiserum was minimally diluted to 1:25.

EXAMPLE X

Immunoglobulins were purified from the raw immune rabbit serum (rabbit #2876 bled day 40 post second immunization and day 14 post third immunization) and the raw immune goat serum (bled day 48 and 85 post second immunization) which had demonstrated best inhibition potential. This was carried out as follows: Antisera were diluted with equal concentrations of (3M) NaCl and (1.5M) glycine buffer (pH 8.9) and filtered through a 0.22 μm MILLISTAK filter (Millipore Corporation, Bedford, Mass.; catalogue number SLGVO25LS). After passing serum over a 15×2.5 cm column (7.5 g Staphylococcus A:SEPHAROSE 4B column gradient; SIGMA, St. Louis, Mo.; catalogue number P3391), it was rinsed with 10–15 volumes of 1.5M NaCl and (0.75M) glycine buffer (pH 8.9). The column was eluted with (0.55M) glycine buffer (pH 3.5) containing 0.85% NaCl. Fractions were immediately neutralized by the addition of (1M) Tris buffer (pH 9.0). Fractions containing antibody were pooled and dialyzed against (0.115M) phosphate buffer (pH 7.4). HPLC analysis of purified antisera confirmed purity of eluted fractions. Recoveries of 2.58 mg/ml of goat anti L-amino acid oxidase antibody and 5.18 mg/ml of rabbit anti L-amino acid oxidase antibody were determined by the method of Lowry, O. H., et al, J. Biol. Chem. 193, 265–275 (1951). Antibody was sterilized by passing through a 0.22 μm Millipore Millex-GV filter and stored at 4° C.

Testing for inhibition of L-amino acid oxidase was carried out by admixing the purified antisera with 30 ng L-amino acid oxidase dissolved in 100 μl of 20 mM Tris, 0.15M NaCl and 10 mM aminotriazole buffer (pH 7.4) containing 0.05% bovine serum albumen.

Maximum inhibition was demonstrated for the purified rabbit antiserum at a concentration of 0.71 μg/μl of 59%.

Maximum inhibition was demonstrated for the purified goat antiserum of 6%.

The percentages are less than in Example IX because some functional immunoglobulin subclasses are apparently lost in the purification.

EXAMPLE XI

Figure 4:
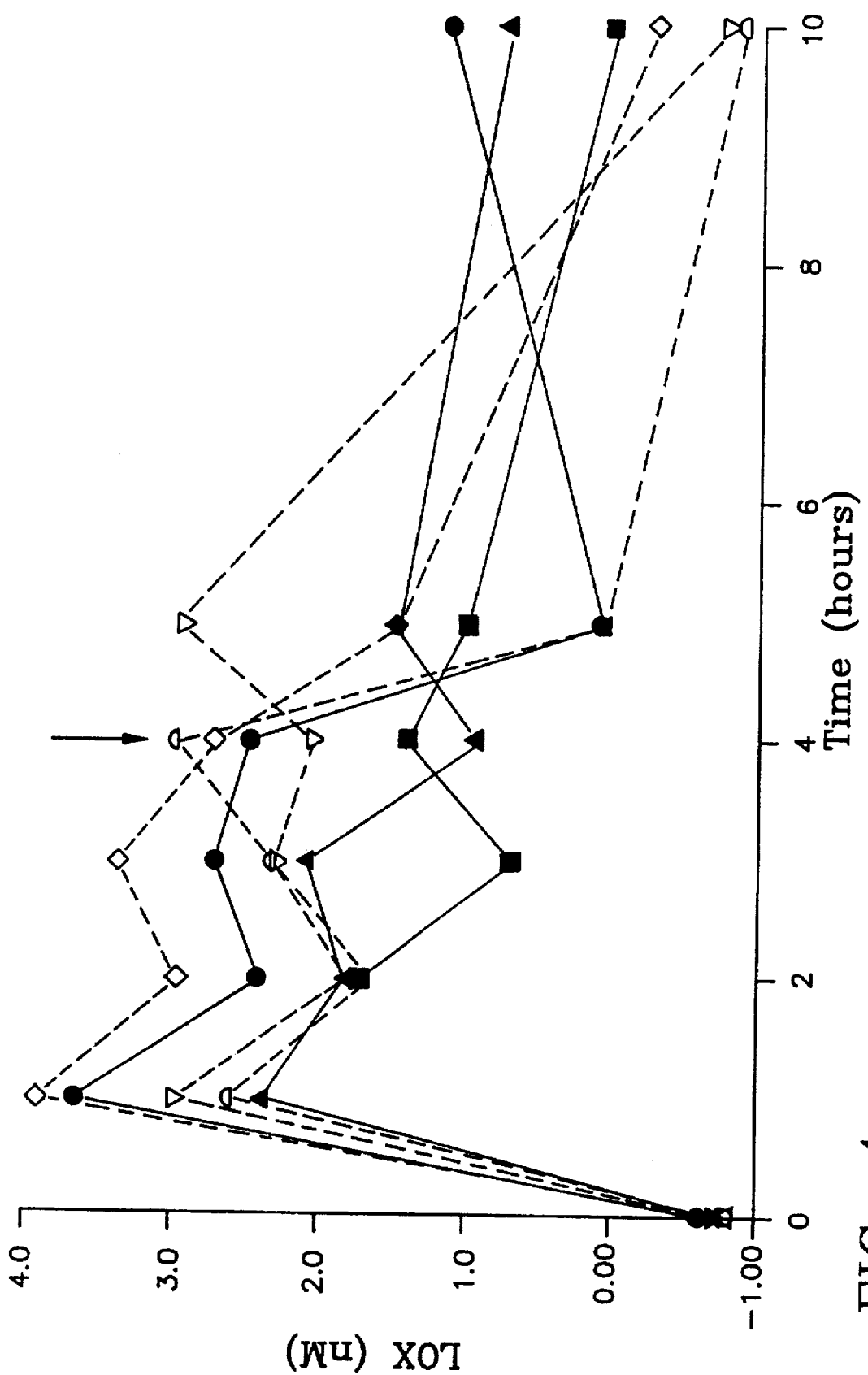
FIG. 4. depicts graphs of time (hours) vs. LOX (nM) and depicts results of Example XI.

L-Amino acid oxidase activity over time was measured in plasma samples from three mice which had been injected intravenously with 200 μg L-amino acid oxidase alone and from three mice intraperitoneally injected with 5000 μg (on a pure antibody basis) of purified rabbit anti L-amino acid oxidase antiserum (prepared as described in Example X) four hours after receiving a 200 μg intravenous L-amino acid oxidase injection. The mice were athymic BALB/C mice (nu/nu genotype, 6 weeks old or older). Assay for L-amino acid oxidase activity was carried out using the $H_2O_2$ PeroXOquant assay described in Example IX. The results are set forth in FIG. 4 wherein "LOX" means L-amino acid oxidase. The filled in symbols and continuous lines denote the results for the mice given L-amino acid oxidase only (where each filled in symbol denotes results for a different one of the three mice given L-Amino acid oxidase only), the open symbols and dashed lines denote the results for the mice given L-amino acid oxidase antiserum and the vertical arrow at 4 hours denotes the time of antiserum (where each open symbol denotes results for a different one of the three mice given L-amino acid oxidase antiserum) administration. As indicated in FIG. 4., L-amino acid oxidase activity decreases over time in both groups with a quicker decrement in the group administered the purified anti L-amino acid oxidase upon the administration thereof. As indicated in FIG. 4, at t=10 hours after L-amino acid oxidase injection, 80.1, 58.6 and 52.3% reductions in L-amino acid oxidase activity were observed in those animals receiving L-amino acid oxidase alone compared to 100.6, 88.92 and 101.0% activity reductions in those animals receiving the purified rabbit anti L-amino acid oxidase antiserum. The percentages greater than 100.0% are considered attributable to standard errors due to pipetting or other steps involved in the determinations.

EXAMPLE XII

The purified goat anti L-amino acid oxidase antiserum of Example X is further purified as follows: L-amino acid oxidase is bound by amino or aldehyde coupling to an HPLC resin. The antibody is passed through a column containing the resin with L-amino acid oxidase bound thereto. The antibody binds to the L-amino acid oxidase. Rinsing is then carried out to remove non specific proteins and bound antibody is eluted with 0.1M sodium citrate (pH 3.0) or 0.1M CAPS buffer (pH 11).

EXAMPLE XIII

Athymic BALB/C mice are injected subcutaneously into the right flank with D-54MG tumors as in Example VI. Four groups of mice are utilized, each containing 10 mice.

Group I is injected intravenously with saline (0.1 to 1 ml) at t=0, intraperitoneally with saline (0.1 to 1 ml) at t=3 hours and intraperitoneally with saline (0.1 to 1 ml) at t=4 hours.

Group II is injected intravenously with saline (0.1 to 1 ml) at t=0 and intraperitoneally with saline (0.1 to 1 ml) at t=3 hours and melphalan is administered intraperitoneally at t=4 hours at a dose of 10 times its $LD_{10}$ dose.

Group III is injected intravenously with 100 µg of L-amino acid oxidase at t=0 and intraperitoneally with saline (0.1 to 1 ml) at t=3 hours and melphalan is administered intraperitoneally at t=4 hours at a dose of 10 times its $LD_{10}$ dose.

Group IV is injected intravenously with 100 µg at L-amino acid oxidase at t=0, intraperitoneally with 100 to 5000 µg (on a pure antibody basis) purified goat anti L-amino acid oxidase antiserum (as produced in Example XI) at t=3 hours and intraperitoneally with melphalan at a dose of 10 times its $LD_{10}$ dose at t=4 hours.

A growth delay of tumors to 5 times pretreatment volume compared to Group I is noted for Group II with increased delay compared to Group II for Group III and increased delay compared to Group III for Group IV.

EXAMPLE XIV

Intracranial D-54MG tumors are grown in BALB/C mice as described in Example VI.

Four groups of mice are utilized each containing 10 mice.

Treatment is carried out the same as in Example XIII.

The median days to death and number of mice surviving is greater for Group II than for Group I, greater for Group III than for Group II and greater for Group IV than for Group III.

Samples of L-amino acid oxidase were determined to have activities ranging from 2.6 to 5.6 units/µg indicating that L-amino acid oxidase used in examples has activity ranging from about 1 to about 8 units/µg.

EXAMPLE XV

Intracranial (IC) D-54 MG tumors were grown in Balb/C mice as described in Example VI.

Treatment groups were control (vehicle), melphalan at 50% of $LD_{10}$ (0.5 melphalan), melphalan at 100% of $LD_{10}$ (1.0 melphalan), melphalan at 50% of $LD_{10}$ plus anti L-amino acid oxidase antibody (0.5 melphalan & AB), melphalan at 50% of $LD_{10}$ plus L-amino acid oxidase (0.5 melphalan and LOX), melphalan at 50% $LD_{10}$ plus anti L-amino acid oxidase antibody plus L-amino acid oxidase (0.5 melphalan & AB & LOX).

The vehicle was saline in an amount of 0.1 to 1 ml.

The L-amino acid oxidase was administered intravenously at a dose of 100 µg.

The anti L-amino acid oxidase antibody was Staphylococcus A purified goat anti L-amino acid oxidase antibody prepared as described in Example X and was administered intraperitoneally in an amount of 0.2 ml (2.53 µg/ml).

The melphalan was administered intraperitoneally at doses of 71 µg/m² (representing 100% of $LD_{10}$) and 35.5 µg/m² (representing 50% of $LD_{10}$).

The results are set forth in Table 7 below.

TABLE 7

| Experiment Number | Groups | time of LOX dose (h) | time of AB dose (h) | time of mel dose (h) | median days to death | % increase survival |
| --- | --- | --- | --- | --- | --- | --- |
| I | 1) 0.5 melphalan | | | 6 | 31.5 | 162.5 |
| | 2) 0.5 melphalan & AB | | 3 | 6 | 27.5 | 129.2 |
| | 3) 0.5 melphalan & LOX | 0 | | 6 | 29 | 141.7 |
| | 4) 0.5 melphalan & AB & LOX | 0 | 3 | 6 | 33 | 175.0 |
| | 5) vehicle | | | | 12 | |
| II | 1) melphalan | | | | 28.5 | 137.5 |
| | 2) 0.5 melphalan & AB & LOX | 0 | 3 | 4 | 32.5 | 170.8 |
| | 3) 0.5 melphalan & AB & LOX | 0 | 3 | 6 | 32 | 166.7 |
| | 4) vehicle | | | | 12 | |
| III | 1) 0.5 melphalan | | | | 27.5 | 111.5 |
| | 2) 1.0 melphalan | | | | 30 | 130.8 |
| | 3) 0.5 melphalan & AB & LOX | 0 | 3 | 4 | 28 | 115.4 |
| | 4) 0.5 melphalan & AB & LOX | 0 | 3 | 5 | 28 | 115.4 |
| | 5) 0.5 melphalan & AB & LOX | 0 | 3 | 6 | 31.5 | 142.3 |
| | 6) 0.5 melphalan & AB & LOX | 0 | 3 | 8 | 28 | 115.4 |
| | 7) 0.5 melphalan & AB & LOX | 0 | 3 | 9 | 27 | 107.6 |
| | 8) vehicle | | | | 13 | |
| IV | 1) 0.5 melphalan | | | | 27 | 68.8 |

TABLE 7-continued

| Experiment Number | Groups | time of LOX dose (h) | time of AB dose (h) | time of mel dose (h) | median days to death | % increase survival |
|---|---|---|---|---|---|---|
| | 2) 1.0 melphalan | | | | 30 | 87.5 |
| | 3) 0.5 melphalan & AB & LOX | 0 | 3 | 6 | 30 | 87.5 |
| | 4) vehicle | | | | 16 | |

As indicated in Table 7, the addition of L-amino acid oxidase and anti-L-amino acid oxidase antibody to melphalan therapy doubled the cytotoxic effect of melphalan at 50% of the $LD_{10}$ to reflect the efficacy of melphalan at 100% of $LD_{10}$. The dosing regimen that consistently achieved this effect was L-amino acid oxidase (100 µg) administered at t=0, followed by anti-L-amino acid oxidase antibody at t=3 hours, followed by melphalan at t=6 hours. No enhancement of cytotoxicity was observed when L-amino acid oxidase or anti-L-amino acid oxidase antibody were used in combination with melphalan administered at 100% of $LD_{10}$.

EXAMPLE XVI

A 20 year old male presenting with symptoms of tremor, stiff hands, and funny ("cogwheel") gait is diagnosed by clinical examination as having idiopathic Parkinson's disease. Dosage of levodopa/carbidopa of 400/100 mg/day are built up to. This is 50% less than the average dosage for normal treatment. The administration of levodopa/carbidopa is preceded each day by administration of 25 units/ml of plasma of L-amino acid oxidase. The L-amino acid oxidase is administered intravenously 15 hours before the administration of the levodopa/carbidopa. Lessening of symptoms is noted.

Similar results to those obtained above are obtained when L-amino acid oxidase is administered 6 hours before the levodopa/carbidopa and 3 µg anti L-amino acid oxidase antibody per unit of L-amino acid oxidase is administered by bolus injection 3 hours after administration of L-amino acid oxidase.

EXAMPLE XVII

A 40 year old female presents with symptoms of headaches, inability to look upward and vomiting and is diagnosed by magnetic resonance imaging as having pineoblastoma brain tumor. Daily treatment consists of administration of 35 units/ml of plasma of L-amino acid oxidase intravenously followed at 12 hours by intravenous administration of 0.3 mg/kg of L-DON. After 7 days of treatment, the following amelioration of symptoms is noted: ability to look upward and less vomiting.

When L-amino acid oxidase is administered 5 hours before L-DON and 3 µg anti L-amino acid oxidase antibody per unit of L-amino acid oxidase is administered 2 hours after the administration of the L-amino acid oxidase, similar results to those obtained above are obtained.

When L-buthionine-S-sulfoximine is administered orally 3 hours before each administration of L-DON, the dosage of L-DON can be reduced to 0.1 mg/kg with the same results.

EXAMPLE XVIII

A patient presents with symptoms of headaches, vomiting and ataxic gait and is diagnosed by magnetic resonance imaging as having medulloblastoma brain tumor. Daily treatment consists of administration of 35 units/ml of plasma of L-amino acid oxidase intravenously followed in 12 hours by administration of 0.3 mg/kg of L-DON intravenously. After 7 days of treatment, amelioration of symptoms is noted. When L-amino acid oxidase is administered 5 hours before L-DON and 3 µg anti-L-amino acid oxidase antibody per unit of L-amino acid oxidase is administered 2 hours after the administration of the L-amino acid oxidase, similar results of amelioration of symptoms are obtained.

EXAMPLE XIX

A patient presents with symptoms of headaches, seizures and left sided weakness and is diagnosed by magnetic resonance imaging as having glioblastoma multiforme. Daily treatment consists of administration of 35 units/ml of plasma of L-amino acid oxidase intravenously followed in 10 hours by administration of 30 mg/kg of acivicin intravenously. After 7 days of treatment, amelioration of symptoms is noted. When L-amino acid oxidase is administered 5 hours before acivicin and 3 µg anti-L-amino acid oxidase antibody per unit of L-amino acid oxidase is administered 3 hours after the administration of L-amino acid oxidase, similar amelioration of symptoms is noted.

EXAMPLE XX

A patient presents with symptoms of headaches, vomiting and double vision and is diagnosed by magnetic resonance imaging as having a germinoma. Daily treatment consists of 35 units/ml of plasma of L-amino acid oxidase intravenously followed in 5 hours by administration of 30 µg/kg of acivicin intravenously. After 7 days of treatment, amelioration of symptoms is noted. When L-amino acid oxidase is administered 7 hours before acivicin and 3 µg anti-L-amino acid oxidase antibody per unit of L-amino acid oxidase is administered 5 hours after the administration of L-amino acid oxidase, similar amelioration of symptoms is noted.

EXAMPLE XXI

A patient presents with symptoms of headaches, seizures and vomiting and is diagnosed by magnetic resonance imaging as having anaplastic astrocytoma. Daily treatments consist of 35 units/ml of plasma of L-amino acid oxidase intravenously followed in 5 hours by administration of 10 µg/kg of azaserine intravenously. After 7 days of treatment, amelioration of symptoms is noted. When L-amino acid oxidase is administered 5 hours before azaserine and 3 µg anti-L-amino acid oxidase antibody per unit of L-amino acid oxidase is administered 2 hours after the administration of the L-amino acid oxidase, similar results of amelioration of symptoms are obtained.

EXAMPLE XXII

A patient presents with symptoms of headaches, vomiting and double vision and is diagnosed by magnetic resonance imaging as having choriocarcinoma. Daily treatments consist of 35 units/ml of plasma of L-amino acid oxidase intravenously followed in 5 hours by administration of 1000 mg/m² of L-alanosine intravenously. After 7 days of treatment, amelioration of symptoms is noted. When L-amino acid oxidase is administered 5 hours before L-alanosine and 3 µg anti-L-amino acid oxidase antibody per unit of L-amino acid oxidase is administered 2 hours after administration of the L-amino acid oxidase, similar results of amelioration of symptoms are obtained.

EXAMPLE XXIII

In Example XVI, instead of levodopa/carbidopa, 5-(1-naphthyl)-3-(phosphonomethyl) phenylalanine (S-configuration), prepared as described in Li, J.-H., et al., J. Med. Chem. 38, 1955–1965 (1995), is administered orally at a dose of 8 mg/kg 12 hours after L-amino acid oxidase is administered intravenously at a dosage of 25 units/ml of plasma. Tremor suppression lasting 12 hours is noted.

Similar results to those obtained above are obtained when L-amino acid oxidase is administered 6 hours before the 5-(1-naphthyl)-3-(phosphonomethyl) phenylalanine and 3 µg anti L-amino acid oxidase antibody per unit of L-amino acid oxidase is administered by bolus injection 3 hours after administration of L-amino acid oxidase.

EXAMPLE XXIV

A patient is diagnosed by magnetic resonance imaging as having supratentorial high grade glioma brain tumor. Daily treatment consists of 35 units/ml of plasma of L-amino acid oxidase administered intravenously followed in 3 hours by administration orally of L-buthionine-S-sulfoximine. After 5 days, radiation therapy is implemented using a linear accelerator at a total dose of 5400 cGy at a rate of 180 cGY/day in 30 fractions over 30 days. Survival 10% longer than the average survival in the case of radiation therapy of glioma is noted.

Enzymes which may be substituted for L-amino acid oxidase in the methods herein include amino acid decarboxylases directed at amino acids transported by the large neutral amino acid carrier, and phenylalanine ammonia lyase.

Many variations of inventive embodiments will be obvious to those skilled in the art. Thus, the inventive embodiments are defined by the claims.

What is claimed is:

1. A method of treatment of a patient for a brain associated disease susceptible to a large neutral amino acid drug, said method comprising:
   (a) administering L-amino acid oxidase to said patient at a dosage ranging from about 1 to about 100 units/ml of plasma, which is non-toxic and which is sufficient to reduce the plasma level of large neutral amino acids from a normal level to a large neutral amino acid drug transport improving level,
   (b) administering orally or parenterally a therapeutically effective amount of the large neutral amino acid drug to said patient wherein the plasma level of large neutral amino acids is reduced from the normal level, within about 2 to 36 hours after administering L-amino acid oxidase;
   thereby to enhance transport of the large neutral amino acid drug across the blood brain barrier compared to where L-amino acid oxidase is not administered.

2. The method of claim 1, wherein the dosage of L-amino acid oxidase administered in step (a) ranges from about 10 to 50 units/ml of plasma and the administration of step (b) is carried out from 12 to 30 hours after the administration of step (a).

3. The method of claim 1 comprising, between the administering of step (a) and the administering of step (b), preventing replenishment of large neutral amino acids to the plasma wherein preventing replenishment comprises causing said patient to fast or administering to said patient a protein-free diet or a combination of both.

4. The method of claim 1 wherein the disease is idiopathic Parkinson's disease, postencephalitic parkinsonism or symptomatic parkinsonism and the drug is levodopa administered with or without carbidopa.

5. The method of claim 1 wherein the disease is a brain tumor susceptible to the large neutral amino acid drug.

6. The method of claim 5 wherein the drug is selected from the group consisting of 6-diazo-5-oxo-norleucine, L-azaserine and acivicin.

7. The method of claim 6 wherein the drug is administered after administration of a glutathione depleting effective amount of a large neutral amino acid glutathione depleting agent which is not metabolized by L-amino acid oxidase.

8. The method of claim 1 wherein the drug is administered after administration of a glutathione depleting effective amount of a large neutral amino acid glutathione depleting agent which is not metabolized by L-amino acid oxidase.

9. The method of claim 1 wherein the drug is an S-configuration 3-(phosphonomethyl)phenylalanine.

10. The method of claim 1 wherein the brain associated disease is selected from the group consisting of acute ischemic events, neurodegenerative disorders and brain tumors.

11. A method of treatment of a patient for a brain associated disease susceptible to a large neutral amino acid drug, said method comprising:
   (a) administering L-amino acid oxidase to said patient at a dosage ranging from about 1 to about 100 units/ml of plasma, which is non-toxic and which is sufficient to reduce the plasma level of large neutral amino acids from a normal level to a large neutral amino acid drug transport improving level,
   (b) administering to the patient wherein the plasma level of large neutral amino acids is reduced from the normal level and from about 1 to 30 hours after the administering in step (a), from about 1 to about 25 µg anti L-amino acid oxidase antibody per unit of L-amino acid oxidase administered in step (a) to inhibit plasma L-amino acid oxidase activity so that the plasma L-amino acid oxidase activity is less than 25% of the plasma L-amino acid oxidase activity one hour after the administration of step (a),
   (c) administering orally or parenterally a therapeutically effective amount of the large neutral amino acid drug to the patient wherein the plasma level of large neutral amino acids is reduced from the normal level, within about 1 to 10 hours after the administration in step (b) and within about 2 to 36 hours after the administration in step (a);
   thereby to enhance transport of the large neutral amino acid drug across the blood brain barrier compared to where L-amino acid oxidase is not administered.

12. The method of claim 11 herein the brain associated disease is selected from the group consisting of acute ischemic events, neurodegenerative disorders and brain tumors.

13. The method of claim 11 wherein the dosage of L-amino acid oxidase administered in step (a) ranges from about 10 to 50 units/ml of plasma.

14. The method of claim 13, wherein the anti L-amino acid oxidase antibody is administered in step (b) at a dosage ranging from about 1 to about 5 µg anti L-amino acid oxidase antibody per unit of L-amino acid oxidase administered in step (a), and the administration of step (b) is carried out from about 1½ to about 6 hours after the administration of step (a) and the administration of step (c) is carried out from about 1 to 10 hours after the administration of step (b) and from about 2½ to 20 hours after the administration of step (a).

15. The method of claim 11 wherein the disease is idiopathic Parkinson's disease, postencephalitic parkinsonism or symptomatic parkinsonism and the drug is levodopa administered with or without carbidopa.

16. The method of claim 11 wherein the disease is a brain tumor susceptible to the large neutral amino acid drug.

17. The method of claim 14 wherein the drug is selected from the group consisting of 6-diazo-5-oxo-norleucine, L-azaserine and acivicin.

18. The method of claim 17 wherein the drug is administered after administration of a glutathione depleting effective amount of a large neutral amino acid glutathione depleting agent which is not metabolized by L-amino acid oxidase.

19. The method of claim 10 wherein the drug is an S-configuration 3-(phosphonomethyl)phenylalanine.

20. The method of claim 19 wherein the drug is administered after administration of a glutathione depleting effective amount of a large neutral amino acid glutathione depleting agent which is not metabolized by L-amino acid oxidase.

21. The method of claim 11 wherein the drug is administered after administration of a glutathione depleting effective amount of a large neutral amino acid glutathione depleting agent which is not metabolized by L-amino acid oxidase.

22. A method of treatment of a patient for a brain tumor which is susceptible to radiation therapy comprising:

(a) on a daily basis, administering L-amino acid oxidase to said patient at a dosage ranging from about 1 to about 100 units/ml of plasma which is non-toxic and which is sufficient to reduce the plasma level of large neutral amino acids from a normal level to a large neutral amino acid glutathione depleting agent transport improving level and administering to the patient wherein the plasma level of large neutral amino acids is reduced from the normal level and from about 1½ to 6 hours after the administration of the L-amino acid oxidase from 20 to 80 mg/kg of large neutral amino acid glutathione depleting agent which is not metabolized by L-amino acid oxidase, and continuing this treatment for as many days as is necessary to deplete glutathione in said tumor, and (b) administering radiation therapy in a tumor volume reducing amount to said tumor wherein glutathione has been depleted.

* * * * *

UNITED STATES PATENT AND TRADEMARK OFFICE
CERTIFICATE OF CORRECTION

PATENT NO. : 5,695,751

DATED : December 9, 1997

INVENTOR(S) : Henry S. Friedman, et al.

It is certified that error appears in the above-identified patent and that said Letters Patent is hereby corrected as shown below:

Claim 17 (column 31, line 15), change "14" to --16--.

Claim 19 (column 31, line 22), change "10" to --11--.

Signed and Sealed this

Third Day of February, 1998

*Attest:*

BRUCE LEHMAN

*Attesting Officer*     *Commissioner of Patents and Trademarks*